(12) United States Patent
Hayashi et al.

(10) Patent No.: US 8,288,003 B2
(45) Date of Patent: Oct. 16, 2012

(54) METHOD FOR PRODUCING PHOSPHORUS-CONTAINING PHENOLIC COMPOUND, NOVEL PHOSPHORUS-CONTAINING PHENOL, CURABLE RESIN COMPOSITION, CURED PRODUCT OF THE SAME, PRINTED WIRING BOARD, AND SEMICONDUCTOR SEALING MATERIAL

(75) Inventors: Koji Hayashi, Chiba (JP); Yoshiyuki Takahashi, Chiba (JP); Ichirou Ogura, Chiba (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 13/256,724

(22) PCT Filed: Aug. 5, 2009

(86) PCT No.: PCT/JP2009/063858
§ 371 (c)(1),
(2), (4) Date: Dec. 12, 2011

(87) PCT Pub. No.: WO2010/106698
PCT Pub. Date: Sep. 23, 2010

(65) Prior Publication Data
US 2012/0095156 A1      Apr. 19, 2012

(30) Foreign Application Priority Data

Mar. 18, 2009   (JP) ................................. 2009-066083

(51) Int. Cl.
| | |
|---|---|
| *B32B 27/38* | (2006.01) |
| *C08L 61/00* | (2006.01) |
| *C08L 63/00* | (2006.01) |
| *C08L 85/02* | (2006.01) |
| *C08G 59/62* | (2006.01) |
| *C07F 9/28* | (2006.01) |
| *C07F 9/547* | (2006.01) |
| *H01L 23/29* | (2006.01) |

(52) U.S. Cl. ......... 428/413; 257/793; 428/901; 523/400; 525/523; 525/534; 525/538; 528/129; 528/153; 528/158; 568/12; 568/17

(58) Field of Classification Search ....................... None
See application file for complete search history.

(56) References Cited

U.S. PATENT DOCUMENTS
| | | | |
|---|---|---|---|
| 6,992,151 B2 | 1/2006 | Wang et al. | |
| 2002/0032279 A1 | 3/2002 | Hwang et al. | |

FOREIGN PATENT DOCUMENTS
| | | | |
|---|---|---|---|
| JP | 60-126293 A | 7/1985 | |
| JP | 5-214070 A | 8/1993 | |
| JP | 11-166035 A | 6/1999 | |
| JP | 2000-80251 A | 3/2000 | |
| JP | 2001-220427 A | 8/2001 | |
| JP | 2001354685 A | * 12/2001 | |
| JP | 2002-37852 A | 2/2002 | |

OTHER PUBLICATIONS

Machine translation of JP 2001354685 A, provided by the JPO website (no date).*
Derwent abstract of JP 2001354685 A (2002).*

* cited by examiner

*Primary Examiner* — Michael J Feely
(74) *Attorney, Agent, or Firm* — McDermott Will & Emery LLP

(57) ABSTRACT

Provided are a method for producing a phosphorus-containing phenolic compound in which reactivity is considerably excellent in the reaction between a phosphorus-containing compound and an aromatic nucleus of a phenol; in the case of using a polyhydric phenol or a phenolic resin as the phenol, a novel phosphorus-containing phenolic compound that serves as a curing agent for an epoxy resin and imparts excellent heat resistance to a cured product; a curable resin composition containing the novel phosphorus-containing phenolic compound; a cured product of the curable resin composition; a printed wiring board; and a semiconductor sealing material. An aromatic aldehyde (a1) having an alkoxy group as a substituent on an aromatic nucleus is allowed to react with an organic phosphorus compound (a2) intramolecularly having a P—H group or a P—OH group. The resultant reaction product is then allowed to react with a phenol (a3).

15 Claims, 3 Drawing Sheets

FIG. 1
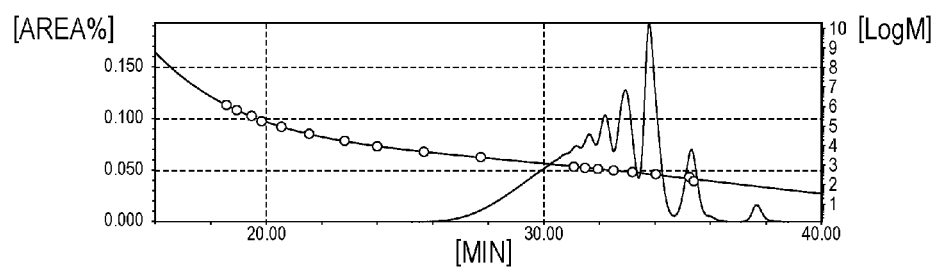
FIG. 2
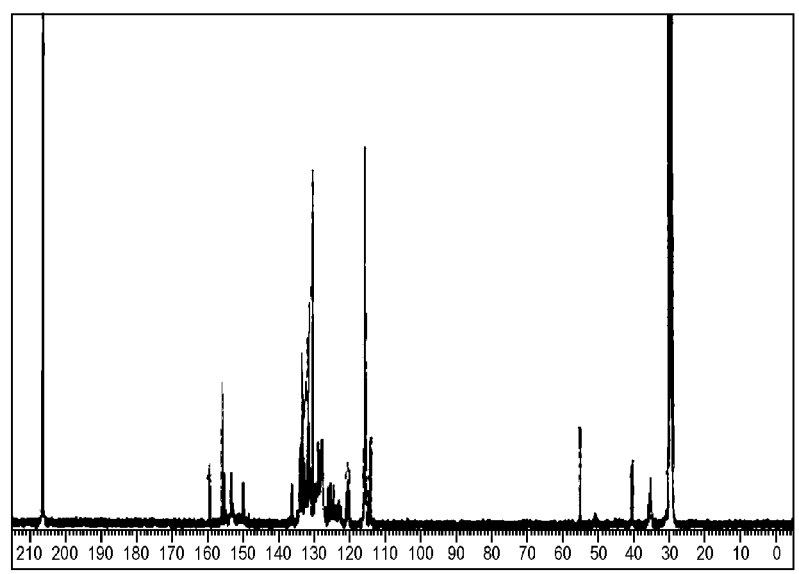
FIG. 3

METHOD FOR PRODUCING PHOSPHORUS-CONTAINING PHENOLIC COMPOUND, NOVEL PHOSPHORUS-CONTAINING PHENOL, CURABLE RESIN COMPOSITION, CURED PRODUCT OF THE SAME, PRINTED WIRING BOARD, AND SEMICONDUCTOR SEALING MATERIAL

CROSS REFERENCE TO PRIOR APPLICATIONS

This application is a U.S. National Phase application under 35 U.S.C. §371 of International Application No. PCT/JP2009/063858, filed on Aug. 5, 2009 and claims benefit of priority to Japanese Patent Application No. 2009-066083, filed on Mar. 18, 2009. The International Application was published in Japanese on Sep. 23, 2010 as WO 2010/106698 A1 under PCI Article 21(2). The contents of the applications are hereby incorporated by reference.

TECHNICAL FIELD

The present invention relates to a method for producing a phosphorus-containing phenolic compound in which a phosphorus atom can be readily introduced into the molecular structure of a phenolic compound and a cured product of the resultant phosphorus-containing phenolic compound or phenolic resin has excellent, fire retardancy and heat resistance; a novel phosphorus-containing phenolic compound; a curable resin composition containing such a novel phosphorus-containing phenolic compound; a cured product of such a curable resin composition; a printed wiring board; and a semiconductor sealing material.

BACKGROUND ART

Epoxy resins and epoxy resin compositions containing curing agents as essential components have high heat resistance and are excellent in terms of various properties such as moisture resistance and hence are widely used for, for example, semiconductor sealing materials, electronic components such as printed circuit hoards, the electronic component field, conductive adhesives such as conductive pastes, other adhesives, matrices for composite materials, coating materials, photoresist materials, and development materials.

In recent years further enhancement of properties represented by heat resistance, moisture resistance, and solder resistance has been demanded in such various applications, in particular, applications to advanced materials. Vehicle-mounted electronic devices that are particularly required to have high reliability and were mounted within cabins have come to be mounted within engine compartments having a higher temperature than cabins. In addition, reflowing treatment temperature has increased due to use of lead-free solders. Accordingly, there is an ever increasing demand for materials having excellent heat resistance.

When epoxy resin compositions are used as materials for printed wiring hoards, to impart fire retardancy to epoxy resin compositions, the compositions are mixed with fire retardants containing halogen such as bromine together with antimony compounds. However, with efforts in terms of environment and safety in recent years, there has been a strong demand for the development of a environmentally friendly and safe method for making compositions have fire retardancy without halogen fire retardants that may emit dioxins and without antimony compounds that may cause cancer. In addition, in the field of materials for printed wiring boards, use of halogen fire retardants causes degradation of reliability of printed wiring boards left to stand at a high temperature. Accordingly, halogen-free compositions are highly expected.

As for an epoxy resin composition that satisfies such required characteristics and has fire retardancy and high heat resistance, for example, Patent Literature 1 described below discloses a technique of using, as a curing agent for epoxy resins, a phosphorus-containing phenolic resin that is obtained as follows: 9,10-dihydro-9-oxa-10-phosphaphenanthrene-10-oxide (hereafter, abbreviated as "HCA") is allowed to react with formaldehyde or acetone to provide a phosphorus compound having a hydroxy group and this phosphorus compound is allowed to react with a phenolic resin. However, in the production process of such a phosphorus-containing phenolic resin, reactivity between polyfunctional phenols and HCA and aldehydes low and hence reaction products between HCA and aldehydes remain as unreacted components in the resultant phenolic resin. Accordingly, although the cured product of the resin has high fire retardancy, the cured product is poor in a thermal decomposition property and cannot pass a thermal delamination test (hereafter, abbreviated as "T288 test") that has been thought to be an important evaluation method for lead-free solder implementation in recent years. In addition, due to the above-mentioned low reactivity between the raw materials, the type of usable polyfunctional phenols is limited and the range of designing phosphorus-containing phenolic resins is considerably limited.

Patent Literature 2 described below discloses, as an intermediate phenolic compound of a phosphorus-containing epoxy resin, a compound obtained by allowing reaction products between HCA and hydroxybenzaldehyde to react with phenol.

However, as for this phenolic compound, reactivity between phenol and reaction products between HCA and hydroxybenzaldehyde is also insufficient and the degree of freedom with which the resin is designed is low. In addition, the finally obtained phenolic compound has a melting point of 200° C. or more and it is difficult to industrially produce this compound. Furthermore, the phenolic compound is a crystalline substance and has a poor dissolution property in organic solvents. Accordingly, the phenolic compound is poor in processability when being handled.

Patent Literature 3 described below discloses a fire-retardant epoxy resin composition in which a phosphorus-modified epoxy resin obtained by allowing a phenolic novolac epoxy resin or a cresol novolac epoxy resin to react with HCA is used as a basic resin and is mixed with a curing agent for an epoxy resin. However, to introduce phosphorus atoms into the structure of the epoxy resin, HCA is allowed to react with epoxy groups that are supposed to serve as cross-linking points. Accordingly, the epoxy resin composition described in Patent Literature 3 does not achieve a sufficiently high cross-linking density and the cured product has a low glass transition temperature. Thus, the epoxy resin composition is not usable for lead-free solder implementation.

As described above, as a method for imparting fire retardancy to a resin component, a technique of using HCA as a modifying agent for a phenolic resin or an epoxy resin is known. When a phosphorus atom is introduced into a phenolic structure by allowing a reaction product between HCA and an aldehyde or a ketone to react with the aromatic nucleus of the phenolic structure, the reaction product has low reactivity and hence the cured product of the resultant phosphorus-containing phenolic resin has insufficient heat resistance and does not exhibit properties for passing a thermal delamination test (hereafter, abbreviated as "T288 test"). In addition, since the reaction product between HCA and an aldehyde or a ketone has low reactivity, phenols that are usable in reaction with the reaction product are limited. Alternatively, when HCA is allowed to react with epoxy groups of an epoxy resin, the concentration of the epoxy groups decreases and hence a sufficiently high heat resistance cannot also be achieved.

CITATION LIST

Patent Literature

[PTL 1] Japanese Patent No. 3464783
[PTL 2] Japanese Patent No. 3476780
[PTL 3] Japanese Patent No. 3613724

SUMMARY OF INVENTION

Technical Problem

Accordingly, objects of the present invention are to provide a method for producing a phosphorus-containing phenolic compound in which reactivity is considerably excellent in the reaction between a phosphorus-containing compound with the aromatic nucleus of a phenol; in the case of using a polyhydric phenol or a phenolic resin as the phenol, a novel phosphorus-containing phenolic compound that serves as a curing agent for an epoxy resin and imparts excellent heat resistance to a cured product; a curable resin composition containing the novel phosphorus-containing phenolic compound; a cured product of the curable resin composition; a printed wiring board containing the novel phosphorus-containing phenolic compound; and a semiconductor sealing material containing the novel phosphorus-containing phenolic compound.

Solution to Problem

The inventors of the present invention have thoroughly studied on how to achieve the objects. As a result, the inventors have found the following findings. When a phosphorus-containing compound represented by the above-described HCA is allowed to react with an aromatic nucleus of a phenol, by allowing the phosphorus-containing compound to react with an aromatic aldehyde having an alkoxy group as a substituent on the aromatic nucleus and subsequently allowing the resultant reaction product to react with the phenol, the reactivity is considerably enhanced. In addition, by using a polyhydric phenol or a phenolic resin as the phenol, the heat resistance of a cured product of a novel phosphorus-containing phenolic compound that is finally obtained is considerably enhanced. Thus, the inventors have accomplished the present invention.

Specifically, the present invention relates to a method for producing a phosphorus-containing phenolic compound including allowing an aromatic aldehyde (a1) having an alkoxy group as a substituent on an aromatic nucleus to react with an organic phosphorus compound (a2) intramolecularly having a P—H group or a P—OH group; and subsequently allowing a resultant reaction product to react with a phenol (a3).

The present invention further relates to a novel phosphorus-containing phenolic compound obtained by the above-described production method.

The present invention further relates to a novel phenol having a chemical structure represented by a structural formula (I) below,

[Chemical formula 1]

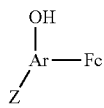

I wherein, in the structural formula (I), Ar represents a benzene ring or a naphthalene ring; Fc represents a hydrogen atom or a hydroxy group; and Z represents a structural unit represented by structural formulae z1 to z4 below,

[Chemical formula 2]

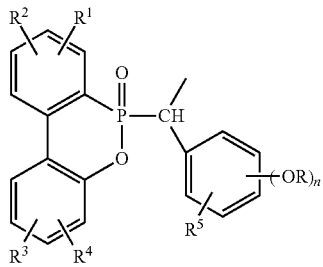

z1

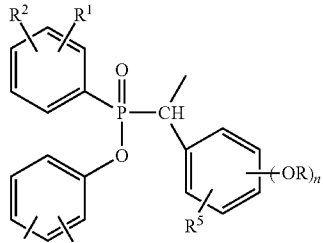

z2

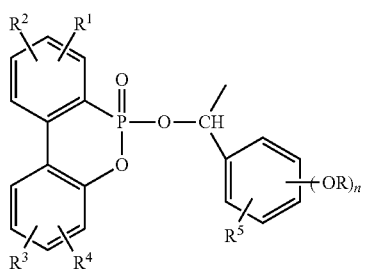

z3

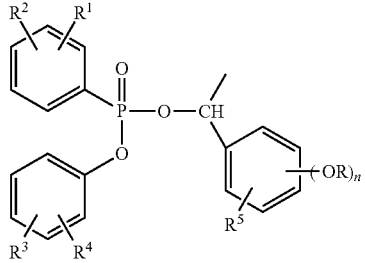

z4

(in the structural formulae z1 to z4, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents a number of a substituent OR on an aromatic nucleus and is 1 to 3).

The present invention further relates to a novel phenolic resin having a novolac phenolic resin structure and having, as a substituent on an aromatic nucleus of the structure, a structural unit represented by structural formulae z1 to z4 below,

[Chemical formula 3]

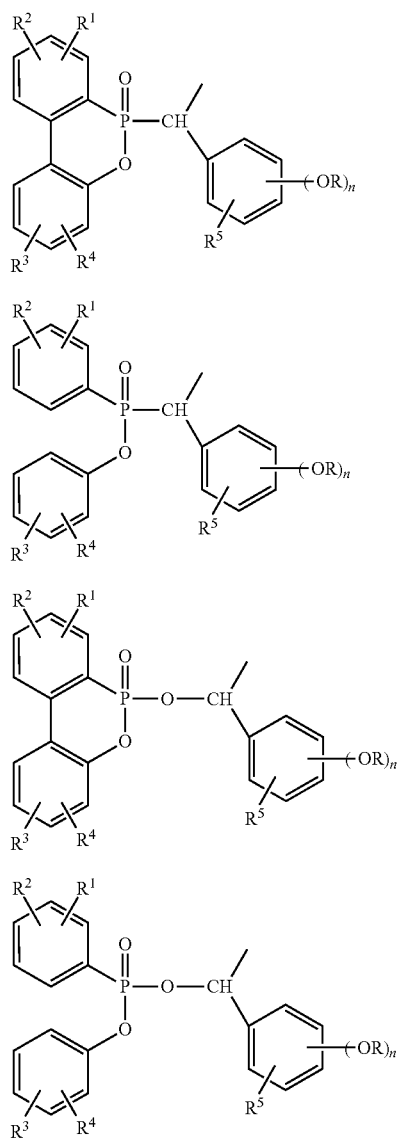

z1 z2 z3 z4

(in the structural formulae z1 to z4, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents a number of a substituent OR on an aromatic nucleus and is 1 to 3).

The present invention further relates to a novel phenol that is a novel phenolic resin including, as a repeating unit, a structure represented by a structural formula (II) below,

[Chemical formula 4]

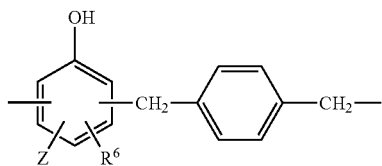

(II)

wherein, in the structural formula (II), $R^6$ represents a hydrogen atom or an alkyl group having 1 to 6 carbon atoms; and Z is selected from the group consisting of a hydrogen atom and structural formulae z1 to z4 below,

[Chemical formula 5]

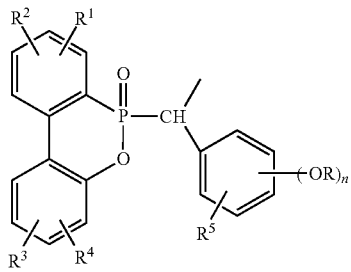

z1

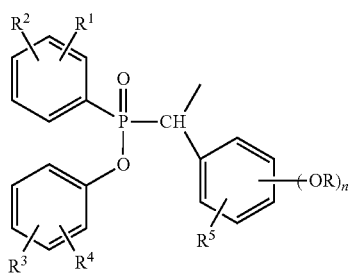

z2

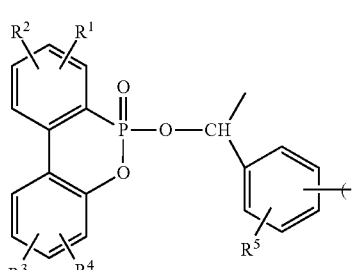

z3

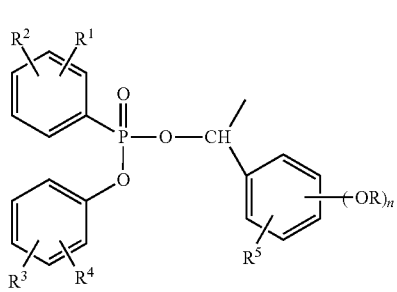

z4

(in the structural formulae z1 to z4, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents a number of a substituent OR on an aromatic nucleus and is 1 to 3) and, in the novel phenolic resin, at least one Z has a structural unit selected from partial structures represented by the structural formulae z1 to z4.

The present invention further relates to a curable resin composition including a phenol (A) and an epoxy resin (B) as essential components, wherein the phenol (A) is the above-described novel phenol.

The present invention further relates to a cured product provided by curing the above-described curable resin composition.

The present invention further relates to a printed wiring board provided by curing a composition containing the phenol (A), the epoxy resin (B), a curing accelerator (C), and an organic solvent (D).

The present invention further relates to a semiconductor sealing material containing the phenol (A), the epoxy resin (B), a curing accelerator (C), and an inorganic filler.

Advantageous Effects of Invention

The present invention provides a method for producing a phosphorus-containing phenolic compound in which reactivity is considerably excellent in the reaction between a phosphorus-containing compound and an aromatic nucleus of a phenol; in the case of using a polyhydric phenol or a phenolic resin as the phenol, a novel phosphorus-containing phenolic compound chat serves as a curing agent for an epoxy resin and imparts excellent heat resistance to a cured product; a curable resin composition containing the novel phosphorus-containing phenolic compound; a cured product of the curable resin composition; a printed wiring board containing the novel phosphorus-containing phenolic compound; and a semiconductor sealing material containing the novel phosphorus-containing phenolic compound.

BRIEF DESCRIPTION OF DRAWINGS

FIG. 1 illustrates a GPC chart of a phenolic resin (A-1) obtained in EXAMPLE 1.

FIG. 2 illustrates a $^{13}$C-NMR spectrum of a phenolic resin (A-1) obtained in EXAMPLE 1.

FIG. 3 illustrates a mass spectrum of a phenolic resin (A-1) obtained in EXAMPLE 1.

DESCRIPTION OF EMBODIMENTS

Figure 4:
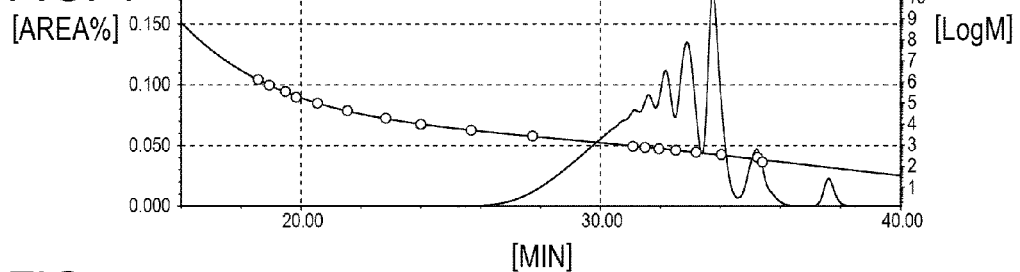
FIG. 4 illustrates a GPC chart of a phenolic resin (A-2) obtained in EXAMPLE 2.

Hereinafter, the present invention will be described in detail.

As described above, a production method according to the present invention includes allowing an aromatic aldehyde (a1) having an alkoxy group as a substituent on an aromatic nucleus to react with an organic phosphorus compound (a2) intramolecularly having a P—H group or a P—OH group; and subsequently allowing the resultant reaction product to react with a phenol (a3).

The aromatic aldehyde (a1) that has an alkoxy group as a substituent on the aromatic nucleus and is used herein is for example, an aromatic aldehyde having an alkoxy group as a substituent on an aromatic nucleus, such as benzaldehyde, o-tolualdehyde, p-tolualdehyde, o-ethylbenzaldehyde, p-ethylbenzaldehyde, isopropylbenzaldehyde, naphthoaldehyde, or anthracene aldehyde. A specific example of the aromatic aldehyde (a1) is a compound. (a1-1) represented by a structural formula (A1-a) below,

[Chemical formula 6]

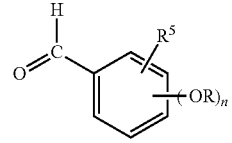

A1-a (in the formula, $R^5$ represents a hydrogen atom or an alkyl group having 1 to 3 carbon atoms; R represents an alkyl group having 1 to 4 carbon atoms; and n represents the number of a substituent OR on the aromatic nucleus and is 1 to 3), or a compound. (a1-2) represented by a structural formula (A1-b) below,

[Chemical formula 7]

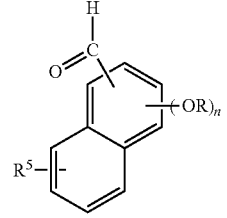

A1-b (in the formula, $R^5$ represents a hydrogen atom or an alkyl group having 1 to 3 carbon atoms; R represents an alkyl group having 1 to 4 carbon atoms; and n represents the number of a substituent OR on the aromatic nucleus and is 1 to 3).

Of these, the compound (A1-a) is particularly preferred (the compound (A1-a) (n=1) is especially preferred) in the present invention because the phosphorus content per molecule is high.

In the present invention, since the aromatic aldehyde (a1) has an alkoxy group as a nucleus substituent, hydroxy groups generated in the reaction product from the aromatic aldehyde (a1) and the organic phosphorus compound (a2) having a P—H group or a P—OH group have excellent reactivity and the product reacts with an aromatic nucleus in the phenol (a3) with little catalyst. The alkoxy group is preferably a methoxy group or an ethoxy group because such an advantage is more significantly exhibited. The aromatic aldehyde is preferably benzaldehyde or naphthoaldehyde.

The organic phosphorus compound (a2) that intramolecularly has a P—H group or P—OH group and reacts with the aromatic aldehyde (a1) may be specifically compound represented by a structural formula (A2-a) or a structural formula (A2-b) below,

[Chemical formula 8]

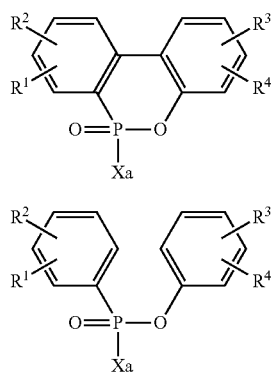

(in the structural formula (212-a) or the structural formula (212-b), Xa represents a hydrogen atom or a hydroxy group; $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group). The alkyl group having 1 to 5 carbon atoms forming $R^1$, $R^2$, $R^3$, and $R^4$ may be a methyl group, an ethyl group, a n-propyl group, an i-propyl group, a t-butyl group, or a n-pentyl group.

In the present invention, Xa in the structural formula (A2-a) or the structural formula (A2-b) preferably represents a hydrogen atom because a compound (X) produced by the reaction with the aromatic aldehyde (a1) has very high reactivity with the phenol (a3). In particular, a compound represented by the structural formula (A2-a) is preferred because a cured product of the phosphorus-containing phenolic compound has excellent fire retardancy. Especially, 9,10-dihydro-9-oxa-10-phosphaphenanthrene-10-oxide is preferably represented by the structural formula (A2-a) in which $R^1$, $R^2$, $R^3$, and $R^4$ all represent a hydrogen atom and Xa represents a hydrogen atom because the compound (X) has very high reactivity and the cured product of a phosphorus-containing phenolic compound that is finally obtained has very high fire retardancy and heat resistance.

The reaction between the aromatic aldehyde (a1) having an alkoxy group as a substituent on the aromatic nucleus and the organic phosphorus compound (a2) having a P—H group or a P—OH group can be performed under a condition, for example, at a temperature of 80 to 180° C. This reaction can be performed in the absence of catalysts or in the presence of a non-ketonic organic solvent such as an alcohol organic solvent or a hydrocarbon organic solvent.

In the case of using a compound represented by the structural formula (a1-1) as the aromatic aldehyde (a1) and using a compound represented by the structural formula (a2-1) or the structural formula (a2-2) as the organic phosphorus compound (a2), examples of the compound (X) produced by such a reaction are represented by the following structural formulae x1 to x4,

[Chemical formula 9]

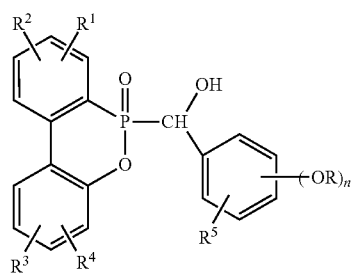

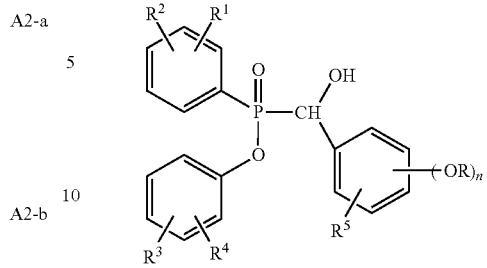

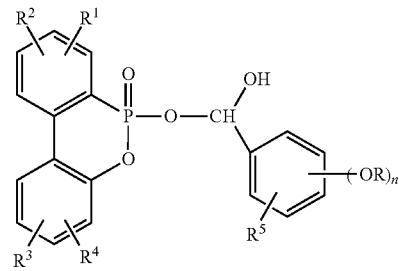

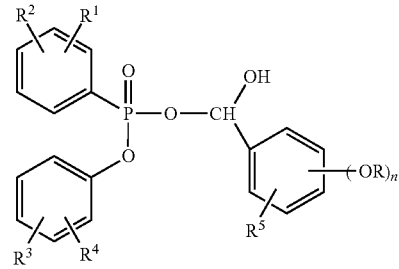

(in the structural formulae x1 to x4, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents the number of a substituent OR on an aromatic nucleus and is 1 to 3).

Of these, compounds represented by the structural formulae x1 and x2 are particularly preferred because these compounds have high reactivity with the phenol (a3). In particular, compounds represented by the structural formula x1 are preferred because the cured product of a phosphorus-containing phenolic compound that is finally obtained has excellent fire retardancy.

Examples of she phenol (a3) used in the present invention include monohydric phenols such as phenol, cresol, xylenol, ethylphenol, isopropylphenol, t-butylphenol, octylphenol, nonylphenol, vinylphenol, isopropenyl phenol, allylphenol, phenylphenol, benzylphenol, chlorophenol, bromophenol, and naphthol; dihydric phenols such as catechol, resorcinol, hydroquinone, 1,5-dihydroxynaphthalene, 1,6-dihydroxynaphthalene, and 2,7-dihydroxynaphthalene; bisphenols such as bisphenol A, bisphenol F, and bisphenol S; phenolic novolac resins, cresol novolac resins, bisphenol A novolac resins, bisphenol S novolac resins, α-naphthol novolac resins, β-naphthol novolac resins, dihydroxynaphthalene novolac resins, in addition, novolac phenolic resins such as novolac resins represented by the following structural formula (A3-a)

[Chemical formula 10]

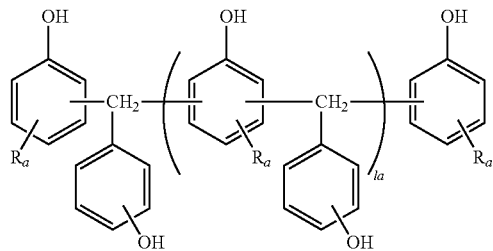

A3-a (in the formula Ra represents a hydrogen atom or a hydrocarbon group having 1 to 6 carbon atoms, and la represents an integer of 0 to 10 in terms of the repeating unit);

phenolic resins having a molecular structure in which phenols are bonded through an alicyclic hydrocarbon group selected from the group consisting of dicyclopentadiene, tetrahydroindene, 4-vinylcyclohexene, 5-vinylnorborna-2-ene, α-pinene, β-pinene, and limonene;

aralkyl phenolic resins represented by the following structural formula (A3-b)

[Chemical formula 11]

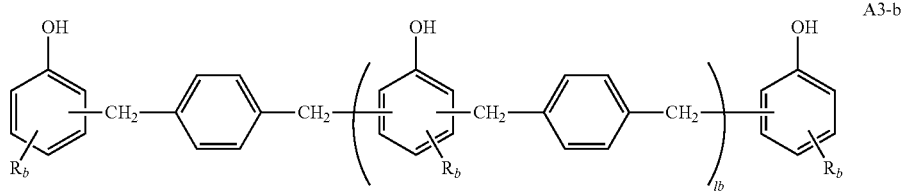

A3-b (in the formula, Rb represents a hydrogen atom or a hydrocarbon group having 1 to 6 carbon atoms, and lb represents an integer of 0 to 10 in terms of the repeating unit);
aralkyl phenolic resins represented by the following structural formula (A3-c)

[Chemical formula 12]

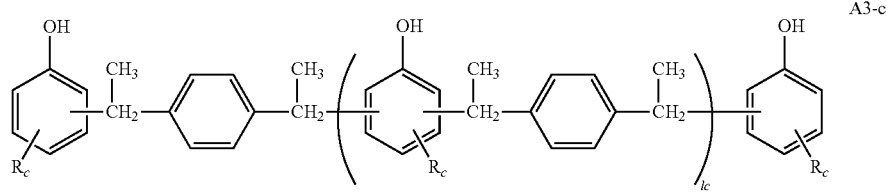

A3-c (in the formula, Rc represents a hydrogen atom or hydrocarbon group having 1 to 6 carbon atoms, and lc represents an integer of 0 to 10 in terms of the repeating unit);
aralkyl phenolic resins represented by the following structural formula (A3-d)

[Chemical formula 13]

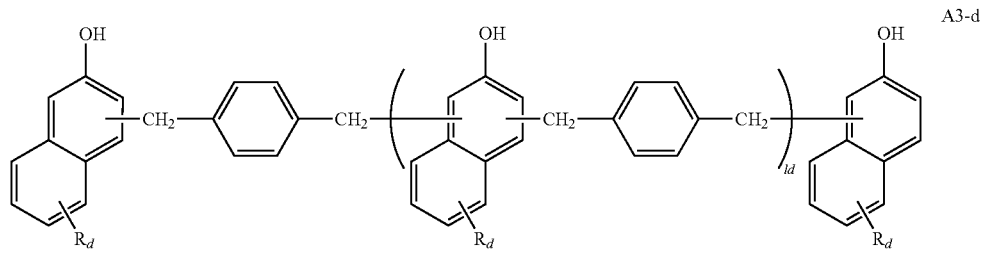

A3-d (in the formula Rd represents a hydrogen atom or a hydrocarbon group having 1 to 6 carbon atoms, and ld represents an integer of 0 to 10 in terms of the repeating unit);
aralkyl phenolic resins represented by the following structural formula (A3-e)

[Chemical formula 14]

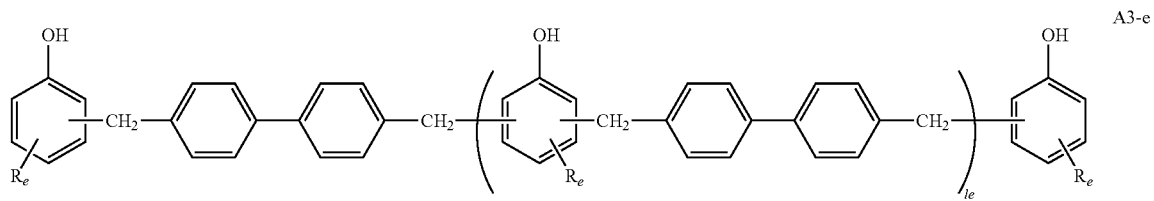

(in the formula, Re represents a hydrogen atom or a hydrocarbon group having 1 to 6 carbon atoms, and le represents an integer of 0 to 10 in terms of the repeating unit);
aralkyl phenolic resins represented by the following structural formula (A3-f)

[Chemical formula 15]

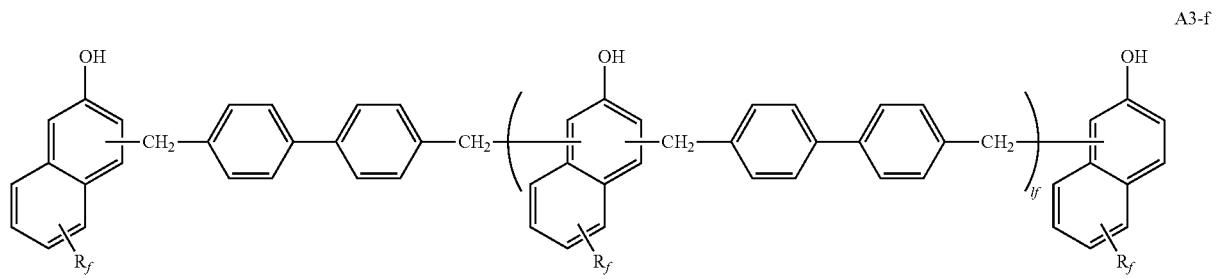

(in the formula, Re represents a hydrogen atom or a hydrocarbon group having 1 to 6 carbon atoms, and lf represents an integer of 0 to 10 in terms of the repeating unit);
aralkyl phenolic resins represented by the following structural formula (A3-g)

[Chemical formula 16]

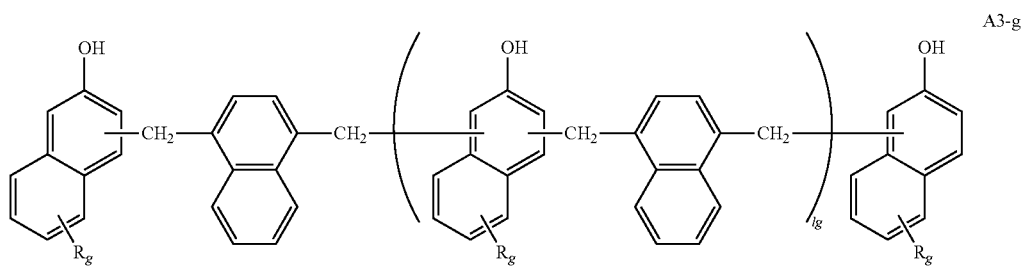

(in the formula, Rg represents a hydrogen atom or a hydrocarbon group having 1 to 6 carbon atoms, and lg represents an integer of 0 to 10 in terms of the repeating unit);
biphenols represented by the following structural formula (A3-h)

[Chemical formula 17]

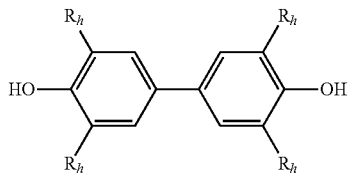

A3-h (in the formula, Rh each independently represents a hydrogen atom or an alkyl group having 1 to 4 carbon atoms); polyhydric naphthols represented by the following structural formula A3-i

[Chemical formula 18]

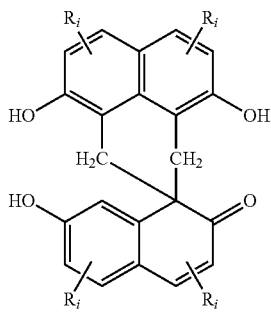

A3-i (in the formula, Ri each independently represents a hydrogen atom or an alkyl group having 1 to 4 carbon atoms); and, when structural units of an aromatic hydrocarbon group having a phenolic hydroxy group (Ph), a fused polycyclic aromatic hydrocarbon group having an alkoxy group (An), and a divalent hydrocarbon group (M) selected from a methylene group, an alkylidene group, and a methylene group having an aromatic hydrocarbon structure (hereafter, simply abbreviated as "methylene group and the like (M)") are respectively denoted by "Ph", "An", and "M", polyfunctional phenols intramolecularly having a structural unit represented by the following partial structural formula (A3-j).

[Chemical formula 19]

-Ph-M-An-     A3j

Specifically, the polyfunctional phenols intramolecularly having a structural unit represented by the partial structural formula A3-h may have structures represented by the following structural formulae (A3-12) and (A3-j3),

[Chemical formula 20]

Ph-M-An-M-Ph-A     A3-j2

An-M-Ph-M-Ph-M-An     A3-j3 novolac structures that have a repeating unit represented by the following structural formula (A3-j4) or (A3-j5)

[Chemical formula 21]

——Ph——M——     A3-j4

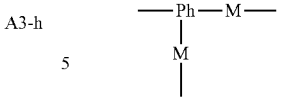

A3-j5 and that have a structure represented by the following structural formula (A3-j6) in molecular ends of the novolac structures, and

[Chemical formula 22]

An-M-     A3-j6 alternating copolymer structures having repeating units represented by the following structural formulae (A3-j7) to (A3-j10).

[Chemical formula 23]

——Ph——M——An——M——     A3-j7

——Ph——M——An——M——
             |
             M
             |     A3-j8

——Ph——M——An——M——
                   |
                   M
                   |     A3-j9

——Ph——M——An——M——
           |            |
           M          M
           |            |     A3j-10

The aromatic hydrocarbon groups having a phenolic hydroxy group (Ph) may have various structures, specifically, preferably, those represented by the following structural formulae Ph1 to Ph16: phenols, naphthols, and aromatic hydrocarbon groups derived from compounds in which the phenols and a naphthol have alkyl groups as substituents on the aromatic nuclei, in view of excellent dielectric properties.

[Chemical formula 24]

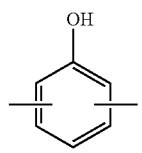

Ph1

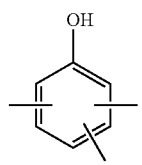

Ph2

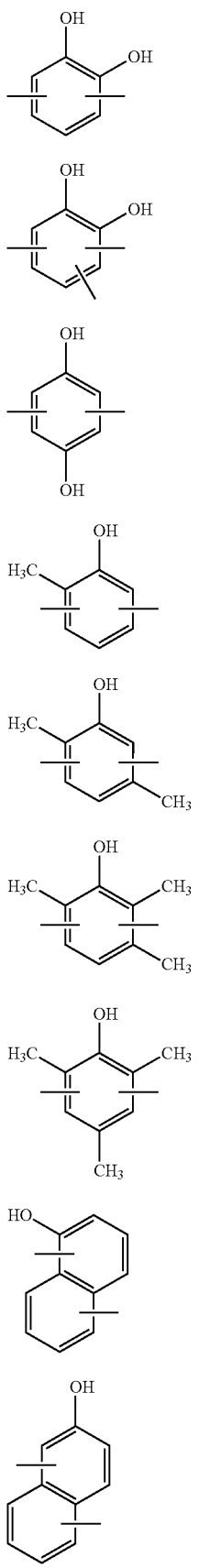
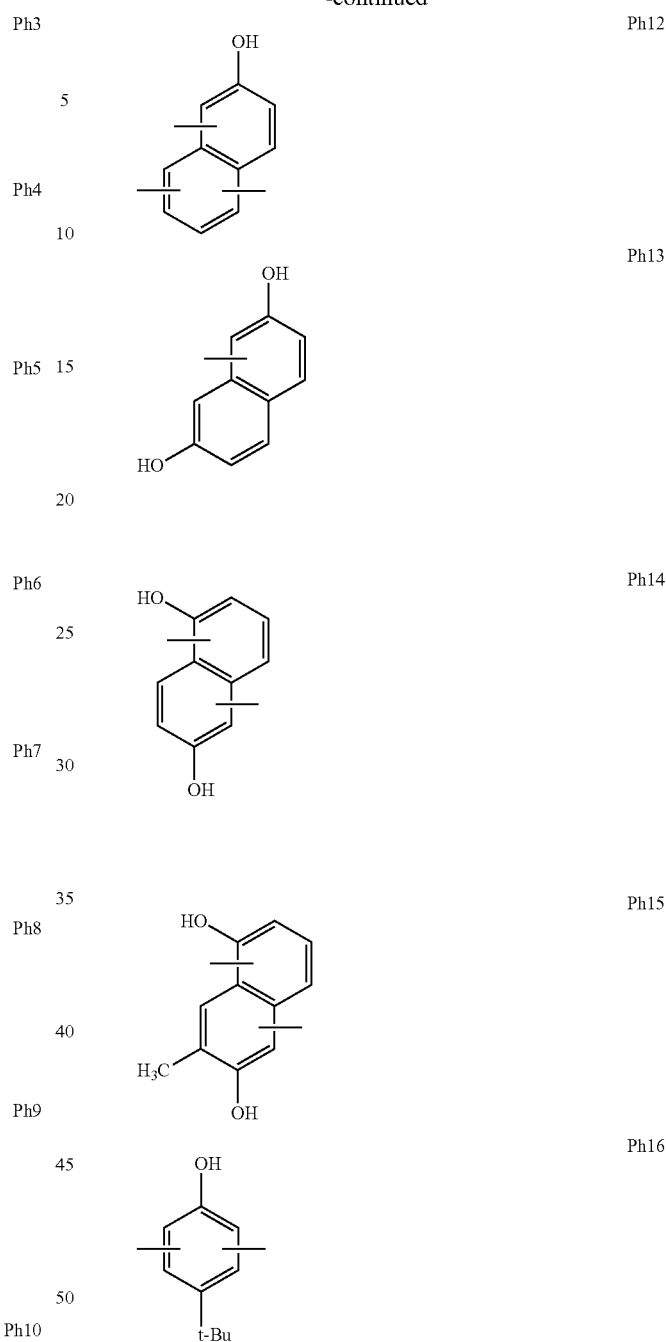

When these structures are at molecular ends, the structures are monovalent aromatic hydrocarbon groups. Among the above-described structures, as for structures that have, on the naphthalene skeletons, two or more bonding sites for other structural units, these bonding sites may be on the same nucleus or different nuclei.

Next, the fused polycyclic aromatic hydrocarbon groups having an alkoxy group (An) included in phenolic resin structures are monovalent or polyvalent aromatic hydrocarbon groups having alkoxy groups as substituents on the fused polycyclic aromatic nuclei. Specifically, An may have alkoxynaphthalene structures represented by the following structural formulae An1 to An12.

[Chemical formula 25]

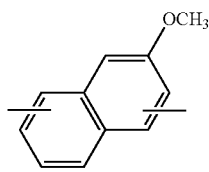 An1

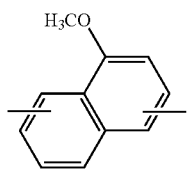 An2

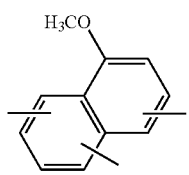 An3

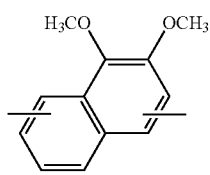 An4

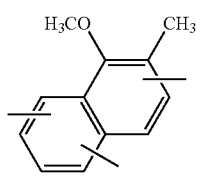 An5

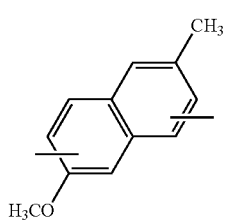 An6

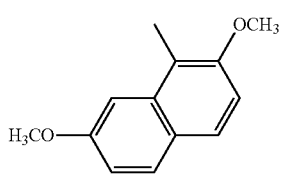 An7

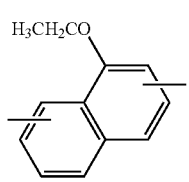 An8

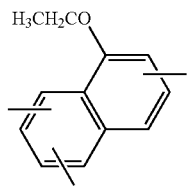 An9

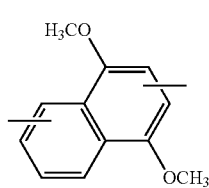 An10

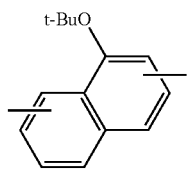 An11

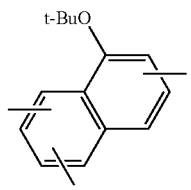 An12

When these structures are at molecular ends, the structures are monovalent aromatic hydrocarbon groups. Among the above-described structures, as for structures that have, on the naphthalene skeletons, two or more bonding sites for other structural units, these bonding sites may be on the same nucleus or different nuclei.

Next, examples of the above-described divalent hydrocarbon group (M) selected from a methylene group, an alkylidene group, and a methylene group having an aromatic hydrocarbon structure include, in addition to a methylene group, alkylidene groups such as an ethylidene group, a 1,1-propylidene group, a 2,2-propylidene group, a dimethylene group, a propane-1,1,3,3-tetrayl group, a n-butane-1,1,4,4-tetrayl group, and a n-pentane-1,1,5,5-tetrayl group. Examples of the methylene group having an aromatic hydrocarbon structure include the following M1 to M8 structures.

[Chemical formula 26]

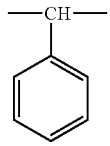 M1

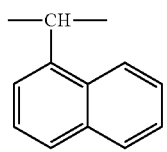 M2

M3
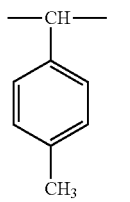

M4
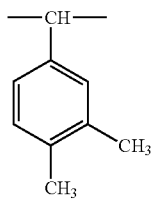

M5
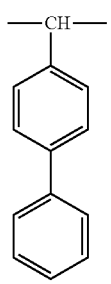

M6
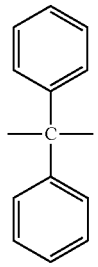

M7
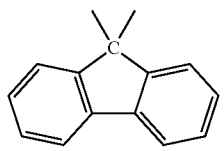

M8
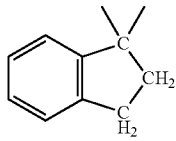

Of these, a methylene group is preferred because, in particular, a methylene group has excellent dielectric effect.

Of these, in the present invention, dihydric phenols, bisphenols novolac phenolic resins, and aralkyl phenolic resins are particularly preferred because, when a reaction product is used as a curing agent for an epoxy resin, the reaction product has good curing properties and dissolution properties in organic solvents. In particular, when the finally obtained phenolic resin is used as an epoxy-resin curing agent for an epoxy resin composition for a printed wiring board, novolac phenolic resins and aralkyl phenolic resins are preferred because these resins are excellent in terms of solvent dissolution properties, moisture resistance, and fire retardancy. In this case, novolac phenolic resins preferably have a melt viscosity at 150° C. in the range of 0.5 to 300 dPa·s in view of moisture resistance, heat resistance, and heat resistance reliability. The aralkyl phenolic resins preferably have a melt viscosity at 150° C. in the range of 0.1 to 300 dPa·s because a cured product of the finally obtained phosphorus-containing phenolic compound is excellent in terms of moisture resistance, heat resistance, and heat resistance reliability. The dihydric phenols are preferably dihydroxynaphthalenes such as 1,5-dihydroxynaphthalene, 1,6-dihydroxynaphthalene, and 2,7-dihydroxynaphthalene because a cured product of the finally obtained phosphorus-containing phenolic compound is excellent in terms of heat resistance.

The reaction between the phenol (a3) and the compound (X), which is a reaction product from the aromatic aldehyde (a1) and the organic phosphorus compound (a2) having a P—H group or a P—OH group, can be performed under a temperature condition of 140 to 200° C. As described above, in the present invention, the reaction between the compound (X) and the phenol (a3) proceeds with very high reactivity and does not particularly need catalysts; however, catalysts may be appropriately used. The catalysts that can be used herein may be inorganic acids such as hydrochloric acid, sulfuric acid, and phosphoric acid; organic acids such as methansulfonic acid, p-toluenesulfonic acid, and oxalic acid; and Lewis acids such as boron trifluoride, anhydrous aluminum chloride, and zinc chloride. The amount of such a catalyst used is preferably less than 5.0 mass % relative to the total weight of raw materials charged.

In the present invention, the reaction proportion between the compound (X) and the phenol (a3) is not particularly limited. On the contrary, due to the high reactivity, the modified amount of the phenol (a3) with respect to the compound (X) can be freely controlled in accordance with a target performance level of fire retardancy or heat resistance or an application. Note that the reaction is preferably performed with a proportion of the compound (X) such that the compound (X) does not remain in a reaction product: specifically, a proportion of the compound (X) is equivalent or less with respect to the reactive points on the aromatic nucleus of the phenol (a3). When the compound (X) is modified with a novolac phenolic resin or an aralkyl phenolic resin that is preferably used as the phenol (a3), the phosphorus content by mass is preferably in the range of 4.0 to 7.0 mass % in view of excellent heat resistance and fire retardancy.

After the reaction, if necessary, dehydration and drying are performed to provide a target substance. In the thus-obtained phosphorus-containing phenolic resin, the compound (X) that is an unreacted component substantially does not remain. For example, when a novolac phenolic resin or an aralkyl phenolic resin is modified with the compound (X) and the phosphorus content by mass is adjusted within the range of 4.0 to 7.0 mass %, the amount of the compound (X) remaining in the phosphorus-containing phenolic resin becomes lower than the lower limit of detection by GPC.

A phosphorus-containing phenolic resin according to the present invention has a molecular structure obtained by the above-described production method. A specific molecular structure can be freely designed by selecting raw material components as described above. For example, the resin may be a novel phenol (np1) having a chemical structure represented by the following structural formula (I),

[Chemical formula 27]

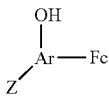

I in the formula (I), Fc represents a hydrogen atom or a hydroxy group and Z represents a structural unit selected from partial structures represented by the following structural formulae z1 to z4,

[Chemical formula 28]

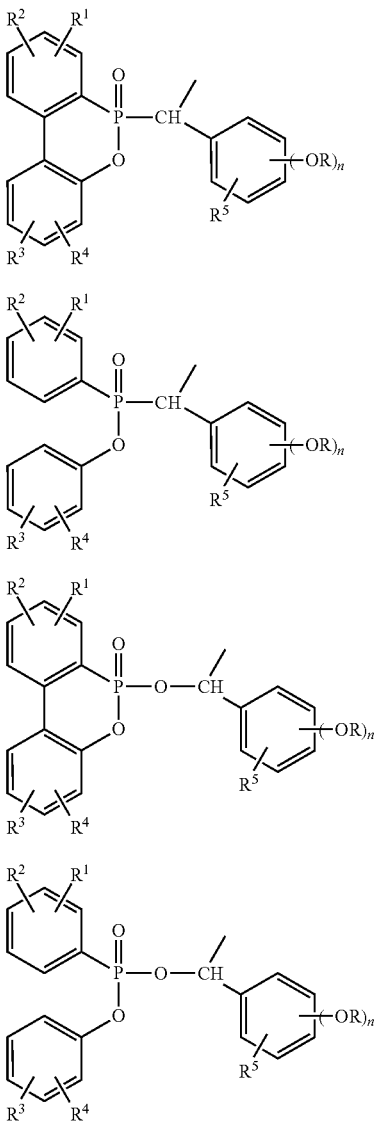

(in the structural formulae z1 to z4, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; R represents a hydrogen atom or an alkyl group having 1 to 5 carbon atoms; R represents an alkyl group having 1 to 4 carbon atoms; and n represents the number of a substituent OR on an aromatic nucleus and is 1 to 3.);

a novel, phenol (np2) having a novolac phenolic resin structure and having, as a substituent on an aromatic nucleus of the structure, the following structural formulae z1 to z4, as a substituent on an aromatic nucleus of the structure, a structural unit selected from the group consisting of partial structures represented by the following structural formulae z1 to z4,

[Chemical formula 29]

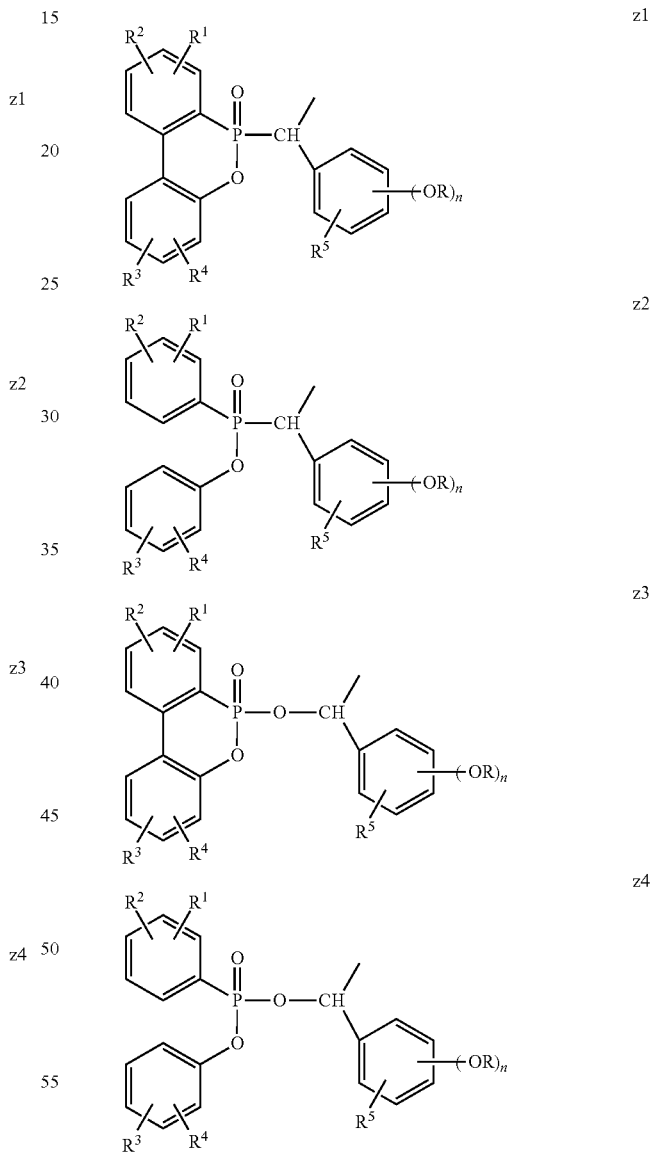

(in the structural formulae z1 to z4, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents the number of a substituent OR on an aromatic nucleus and is 1 to 3.);

a novel phenol (np3) including, as a repeating unit, a structure represented by the following structural formula (II),

[Chemical formula 30]

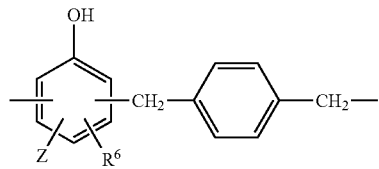
(II)

in the structural formula (II), $R^6$ represents a hydrogen atom or an alkyl group having 1 to 6 carbon atoms; and Z is selected from the group consisting of a hydrogen atom and the following structural formulae z1 to z4,

[Chemical formula 31]

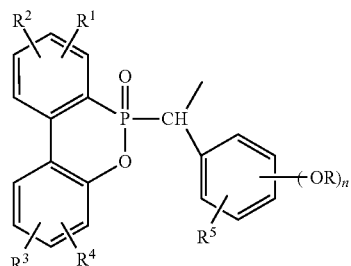
z1

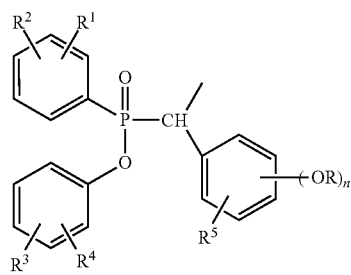
z2

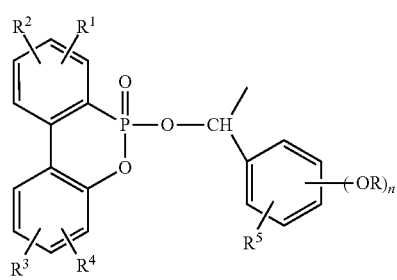
z3

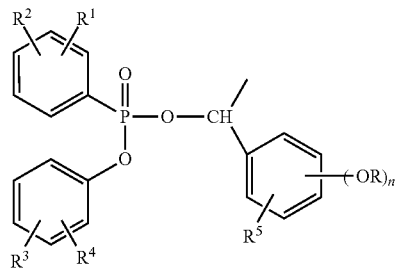
z4

(in the structural formulae z1 to z4, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents the number of a substituent OR on an aromatic nucleus and is 1 to 3) and, in the novel phenolic resin, at least one Z has a structural unit selected from partial structures represented by the structural formulae z1 to z4.

Of these, particularly preferred are phenolic resins having two or more phenolic hydroxy groups, the novel phenol (np2), the novel phenol (np3), and a novel phenol (np1') having a chemical structure represented by the following structural formula (I'),

[Chemical formula 32]

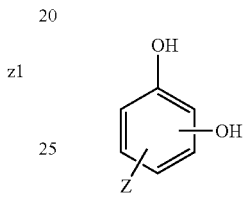
I' where Z in the structural formula (I') is a structural unit represented by the following structural formulae z1 to z4

[Chemical formula 33]

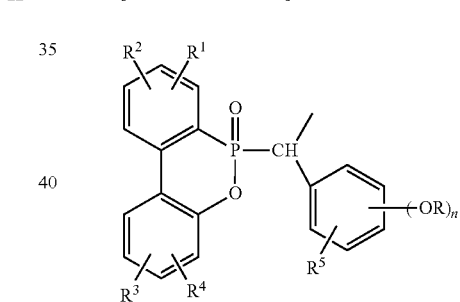
z1

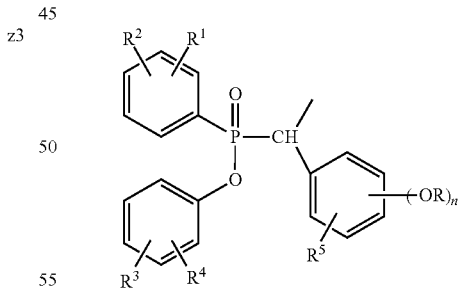
z2

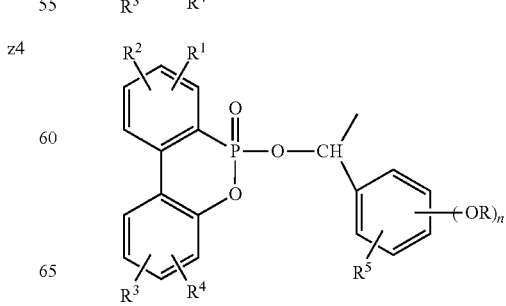
z3

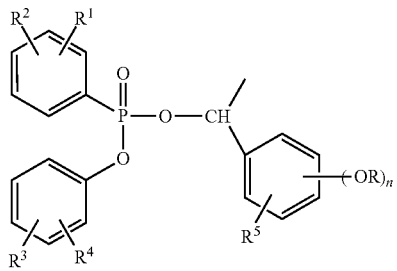

(in the structural formulae z1 to z4, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents the number of a substituent OR on an aromatic nucleus and is 1 to 3).

In the novel phenol (np1), the novel phenol (np2), the novel phenol (np3), and the novel phenol (np1'), among the partial structures represented by the structural formulae z1 to z4, the partial structures represented by the structural formulae z1 and z2 are particularly preferred because cured products have excellent heat resistance and, in particular, the partial structure represented by the structural formula z1 is preferred.

A curable resin composition according to the present invention contains the phenol (A) and the epoxy resin (B) as essential components.

The epoxy resin (B) used herein may be various epoxy resins, for example, a bisphenol epoxy resin such as a bisphenol A epoxy resin or a bisphenol F epoxy resin; a biphenyl epoxy resin such as a biphenyl epoxy resin or a tetramethyl biphenyl epoxy resin; a novolac epoxy resin such as a phenolic novolac epoxy resin, a cresol novolac epoxy resin, a bisphenol A novolac epoxy resin, an epoxidized condensate derived from a phenol and an aromatic aldehyde having a phenolic hydroxy group, or a biphenyl novolac epoxy resin; a triphenylmethane epoxy resin; a tetraphenylethane epoxy resin; a dicyclopentadiene-phenol addition reaction epoxy resin; a phenol aralkyl epoxy resin; an epoxy resin intramolecularly having a naphthalene skeleton such as a naphthol novolac epoxy resin, a naphthol aralkyl epoxy resin, a naphthol-phenol cocondensation novolac epoxy resin, a naphthol-cresol cocondensation novolac epoxy resin, diglycidyloxynaphthalene, or 1,1-bis(2,7-diglycidyloxy-1-naphthyl)alkane; or a phosphorus-containing epoxy resin. These epoxy resins may be used alone or in combination of two or more thereof.

The phosphorus-containing epoxy resin may be, for example, an epoxidized product of 9,10-dihydro-9-oxa-10-phosphaphenanthrene-10-oxide (hereafter, abbreviated as "HCA"), an epoxidized product of a phenolic resin obtained by reaction between HCA and a quinone, an epoxy resin obtained by modifying a phenolic novolac epoxy resin with HCA, an epoxy resin obtained by modifying a cresol novolac epoxy resin with HCA, an epoxy resin obtained by modifying a bisphenol A epoxy resin with a phenolic resin obtained by reaction between HCA and a quinone, or an epoxy resin obtained by modifying a bisphenol F epoxy resin with a phenolic resin obtained by reaction between HCA and a quinone.

Of the above-described epoxy resins (B), novolac epoxy resins and epoxy resins having a naphthalene skeleton in the molecular structure are particularly preferred in view of heat resistance; and bisphenol epoxy resins and novolac epoxy resins are preferred in view of solvent dissolution properties.

In a curable resin composition according no the present invention, as a curing agent for the epoxy resin (B), a curing agent (A') other than the phenolic resin may also be used. Such another curing agent (A') may be an amine compound, an amide compound, an acid anhydride compound, a phenolic compound, or the like. Specific examples of the amine compound include diaminodiphenylmethane, diethylenetriamine, triethylenetetramine, diaminodiphenyl sulfone, isophoronediamine, imidazole, $BF_3$-amine complex, and guanidine derivatives. Specific examples of the amide compound include dicyandiamide and a polyamide resin synthesized from dimers of linolenic acid and ethylenediamine. Specific examples of the acid anhydride compound include phthalic anhydride, trimellitic anhydride, pyromellitic dianhydride, maleic anhydride, tetrahydrophthalic anhydride, methyltetrahydrophthalic anhydride, methylnadic anhydride, hexahydrophthalic anhydride, and methylhexahydrophthalic anhydride. Specific examples of the phenolic compound include polyhydric phenolic compounds such as a phenolic novolac resin, a cresol novolac resin, an aromatic hydrocarbon formaldehyde resin modified phenolic resin, a dicyclopentadiene-phenol adduct resin, a phenol aralkyl resin (xylock resin), a naphthol aralkyl resin, a trimethylolmethane resin, a tetraphenylolethane resin, a naphthol novolac resin, a naphthol-phenol cocondensation novolac resin, a naphthol-cresol cocondensation novolac resin, a biphenyl-modified phenolic resin (a polyhydric phenolic compound in which phenolic nuclei are bonded through bismethylene groups), a biphenyl-modified naphthol resin (a polyhydric naphthol compound in which phenolic nuclei are bonded through bismethylene groups), an aminotriazine-modified phenolic resin (a compound intramolecularly having a phenolic skeleton, a triazine ring, and a primary amino group), and an alkoxy-group-containing aromatic ring modified novolac resin (a polyhydric phenolic compound in which phenolic nuclei and alkoxy-group-containing aromatic rings are bonded through formaldehyde).

Of these, compounds intramolecularly having a large number of aromatic skeletons are particularly preferred in view of low thermal expansion. Specifically, in view of excellent low thermal expansion, preferred are a phenolic novolac resin, a cresol novolac resin, an aromatic hydrocarbon formaldehyde resin modified phenolic resin, a phenol aralkyl resin, a naphthol aralkyl resin, a naphthol novolac resin, a naphthol-phenol cocondensation novolac resin, a naphthol-cresol cocondensation novolac resin, a biphenyl-modified phenolic resin, a biphenyl-modified naphthol resin, an aminotriazine-modified phenolic resin, and an alkoxy-group-containing aromatic ring modified novolac resin (a polyhydric phenolic compound in which phenolic nuclei and alkoxy-group-containing aromatic rings are bonded through formaldehyde).

As for the aminotriazine-modified phenolic resin, that is, a compound intramolecularly having a phenolic skeleton, a triazine ring, and a primary amino group, preferred is a compound having a molecular structure obtained by condensation reaction between a triazine compound, a phenol, and an aldehyde because a cured product has good fire retardancy. In the present invention, by using the compound (A'-b) that has a nitrogen content of 10 to 25 mass %, preferably 15 to 25 mass %, the linear expansion coefficient of a cured product considerably decreases and excellent dimensional stability can be exhibited.

The condensation reaction between a triazine compound, a phenol, and an aldehyde actually provides a mixture of various compounds. Accordingly, the compound (A'-b) is preferably used as the mixture (hereafter, abbreviated as "mixture (A'-b)"). In the present invention, in view of low tip expansion coefficient, the mixture (A'-b) preferably has a nitrogen content in the range of 10 to 25 mass %, in particular, 15 to 25 mass %.

Herein, the term "phenolic skeleton" is a phenolic structural unit derived from a phenol. The term "triazine skeleton" is a triazine structural unit derived from a triazine compound.

The phenols used herein are not particularly limited and examples thereof include phenol; alkyl phenols such as o-cresol, m-cresol, p-cresol, xylenol, ethylphenol, butylphenol, nonylphenol, and octylphenol; polyhydric phenols such as bisphenol A, bisphenol F, bisphenol 5, bisphenol AD, tetramethyl bisphenol A, resorcin, and catechol; naphthols such as monohydroxynaphthalene and dihydroxynaphthalene; phenylphenols; and aminophenols. These phenols may be used alone or in combination of two or more thereof. Phenol is preferred because a final cured product has excellent fire retardancy and phenol has excellent reactivity with amino-group-containing triazine compounds.

Compounds having a triazine ring are not particularly limited and are preferably compounds represented by the following structural formula and isocyanuric acid,

[Chemical formula 34]

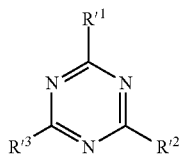

(in the formula, $R'^1$, $R'^2$, and $R'^3$ represent an amino group, an alkyl group, a phenyl group, a hydroxyl group, a hydroxylalkyl group, an ether group, an ester group, an acid group, an unsaturated group, or a cyano group.).

In the compounds represented by the structural formula, amino-group-containing triazine compounds represented by guanamine derivatives such as melamine, acetoguanamine, and benzoguanamine in which two or three of $R'^1$, $R'^2$, and $R'^3$ above represent amino groups are particularly preferred in view of excellent reactivity.

These compounds are also not limited to usage of a single compound and two or more thereof may be used in combination.

The aldehyde is not particularly limited and is preferably formaldehyde in view of ease of handling. Non-limiting representative sources of formaldehyde include formalin and paraformaldehyde.

The amounts of the epoxy resin (B) and the phenol resin (A) in a curable resin composition according to the present invention are not particularly limited. The amounts are preferably set such chat the amount of active hydrogen in the phenol resin (A) is 0.7 to 1.5 equivalents per equivalent of epoxy groups in total of the epoxy resin (B) because the resultant cured product has good characteristics.

If necessary, a curable resin composition according to the present invention may also appropriately contain a curing accelerator. Such curing accelerators may be various curing accelerators and examples thereof include phosphorus compounds, tertiary amines, imidazole, metal salts of organic acids, Lewis acids, and amine complex salts. When the composition is particularly used as a semiconductor sealing material, a preferred phosphorus compound is triphenyl phosphine and a preferred amine compound is 2-ethyl-4-methylimidazole in view of excellent curing properties, heat resistance, electric characteristics, moisture resistance reliability, and the like.

As described above, a curable resin composition according to the present invention having been described so far in detail exhibits excellent solvent dissolution properties. Accordingly, the curable resin composition preferably contains, in addition to the above-described components, an organic solvent (C). Examples of such usable organic solvent (C) include methyl ethyl ketone, acetone, dimethylformamide, methyl isobutyl ketone, methoxy propanol, cyclohexanone, methyl cellosolve, ethyl diglycol acetate, and propylene glycol monomethyl ether acetate. The selection of the solvent and the appropriate amount the solvent used can be appropriately determined on the basis of an application. For example, in applications to printed wiring boards, polar solvents having a boiling point of 160° C. or less such as methyl ethyl ketone, acetone, and 1-methoxy-2-propanol are preferred and the polar solvents are preferably used such that a nonvolatile content is 40 to 80 mass %. In applications to adhesive films for build-up, the organic solvent (C) is preferably a ketone such as acetone, methyl ethyl ketone, or cyclohexanone; an acetate such as ethyl acetate, butyl acetate, cellosolve acetate, propylene glycol monomethyl ether acetate, or carbitol acetate; a carbitol such as cellosolve or butyl carbitol; an aromatic hydrocarbon such as toluene or xylene; dimethylformamide, dimethylacetamide, N-methylpyrrolidone, or the like. In addition, the organic solvent (C) is preferably used such that a nonvolatile content is 30 to 60 mass %.

To make the thermally curable resin composition exhibit fire retardancy, the thermally curable resin composition may be made to contain a non-halogen fire retardant that substantially contains no halogen atoms in, for example, the field of printed wiring boards as long as reliability is not degraded.

Examples of the non-halogen fire retardant include phosphorus fire retardants, nitrogen fire retardants, silicone fire retardants, inorganic fire retardants, and organic metal salt fire retardants. Use of these fire retardants are not limited at all. The fire retardants may be used alone, in combination of fire retardants of the same type, or in combination of fire retardants of different types.

As the phosphorus fire retardants, inorganic and organic fire retardants are usable. Examples of such inorganic compounds include red phosphorus and inorganic nitrogen-containing phosphorus compounds such as ammonium phosphates (e.g., monoammonium phosphate, diammonium phosphate, triammonium phosphate, and ammonium polyphosphate) and phosphoric acid amide.

The red phosphorus is preferably surface-treated for the purpose of suppressing hydrolysis and the like. Examples of such a surface treatment method include (i) a method of applying an inorganic compound such as magnesium hydroxide, aluminum hydroxide, zinc hydroxide, titanium hydroxide, bismuth oxide, bismuth hydroxide, bismuth nitrate, or mixture of the foregoing; (ii) a method of applying a mixture of an inorganic compound such as magnesium hydroxide, aluminum hydroxide, zinc hydroxide, or titanium hydroxide, and a thermosetting resin such as a phenolic resin; and (iii) a method of applying a thermosetting resin such as a phenolic resin to a coating of an inorganic compound such as magnesium hydroxide, aluminum hydroxide, zinc hydroxide, or titanium hydroxide to provide double coatings.

Examples of the organic phosphorus compounds include, in addition to general-purpose organic phosphorus compounds such as phosphoric ester compounds, phosphonic acid compounds, phosphinic acid compounds, phosphine oxide compounds, phospholan compounds, and organic nitrogen-containing phosphorus compounds, cyclic organic phosphorus compounds such as 9,10-dihydro-9-oxa-10-phosphaphenanthrene=10-oxide, 10-(2,5-dihydroxyphenyl)-10H-9-oxa-10-phosphaphenanthrene=10-oxide, and 10-(2,7-dihydroxynaphthyl)-10H-9-oxa-10-phosphaphenanthrene=10-oxide, and derivatives obtained by reactions between the cyclic organic phosphorus compounds and compounds such as epoxy resins and phenolic resins.

The amount of a phosphorus fire retardant added is appropriately selected on the basis of the type of the phosphorus fire retardant, other components in the curable resin composition, and a desired degree of fire retardancy. For example, in 100 parts by mass of a curable resin composition containing all the components such as an epoxy resin, a curing agent, a non-halogen fire retardant, a filler, and additives, when red phosphorus is used as a non-halogen fire retardant, red phosphorus is preferably added in the range of 0.1 to 2.0 parts by mass. Similarly, when an organic phosphorus compound is used, the organic phosphorus compound is preferably added in the range of 0.1 to 10.0 parts by mass, particularly preferably, in the range of 0.5 to 6.0 parts by mass.

When the phosphorus fire retardant is used, the phosphorus fire retardant may be used together with hydrotalcite, magnesium hydroxide, boride compounds, zirconium oxide, black dyes, calcium carbonate, zeolite, zinc molybdate, activated carbon, or the like.

Examples of the nitrogen fire retardants include triazine compounds, cyanuric acid compounds, isocyanuric acid compounds, and phenothiazine; and preferred are triazine compounds, cyanuric acid compounds, and isocyanuric acid compounds.

Examples of the triazine compounds include, in addition to melamine, acetoguanamine, benzoguanamine, melon, melam, succinoguanamine, ethylenedimelamine, melamine polyphosphate, and triguanamine; aminotriazine sulfate compounds such as guanylmelamine sulfate, melem sulfate, and melam sulfate; the above-described aminotriazine-modified phenolic resin; and compounds obtained by further modifying the aminotriazine-modified phenolic resin with tung oil, isomerized linseed oil, or the like.

Specific examples of the cyanuric acid compounds include cyanuric acid and melamine cyanurate.

The amount of such a nitrogen fire retardant added is appropriately selected on the basis of the type of the nitrogen fire retardant, other components in the curable resin composition, and a desired degree of fire retardancy. For example, in 100 parts by mass of a curable resin composition containing all the components such as an epoxy resin, a curing agent, a non-halogen fire retardant, a filler, and additives, the nitrogen fire retardant is preferably added in the range of 0.05 to 10 parts by mass, particularly preferably, in the range of 0.1 to 5 parts by mass.

Such a nitrogen fire retardant may be used together with a metal hydroxide, a molybdenum compound, or the like.

The silicone fire retardants are not particularly limited as long as the silicone fire retardants are organic compounds having silicon atoms. Examples of the silicone fire retardants include silicone oils, silicone rubbers, and silicone resins.

The amount of such a silicone fire retardant added is appropriately selected on the basis of the type of the silicone fire retardant, other components in the curable resin composition, and a desired degree of fire retardancy. For example, in 100 parts by mass of a curable resin composition containing all the components such as an epoxy resin, a curing agent, a non-halogen fire retardant, a filler, and additives, the silicone fire retardant is preferably added in the range of 0.05 to 20 parts by mass. Such a silicone fire retardant may be used together with a molybdenum compound, alumina, or the like.

Examples of the inorganic fire retardants include metal hydroxides, metal oxides, metal carbonate compounds, metal powders, boron compounds, and low-melting glass.

Specific examples of the metal hydroxides include aluminum hydroxide, magnesium hydroxide, dolomite, hydrotalcite, calcium hydroxide, barium hydroxide, and zirconium hydroxide.

Specific examples of the metal oxides include zinc molybdate, molybdenum trioxide, zinc stannate, tin oxide, aluminum oxide, iron oxide, titanium oxide, manganese oxide, zirconium oxide, zinc oxide, molybdenum oxide, cobalt oxide, bismuth oxide, chromium oxide, nickel oxide, copper oxide, and tungsten oxide.

Specific examples of the metal carbonate compounds include zinc carbonate, magnesium carbonate, calcium carbonate, barium carbonate, basic magnesium carbonate, aluminum carbonate, iron carbonate, cobalt carbonate, and titanium carbonate.

Specific examples of the metal powders include powders of aluminum, iron, titanium, manganese, zinc, molybdenum, cobalt, bismuth, chromium, nickel, copper, tungsten, and tin.

Specific examples of the boron compounds include zinc borate, zinc metaborate, barium metaborate, boric acid, and borax.

Specific examples of the low-melting glass include CEEPREE (Bokusui Brown Co., Ltd.), hydrated glass $SiO_2$—$MgO$—$H_2O$, and glass compounds of $PbO$—$B_2O_3$, $ZnO$—$P_2O_5$—$MgO$, $P_2O_5$—$B_2O_3$—$PbO$—$MgO$, $P$—$Sn$—$O$—$F$, $PbO$—$V_2O_5$—$TeO_2$, $Al_2O_3$—$H_2O$, and lead borosilicate.

The amount of such an inorganic fire retardant added is appropriately selected on the basis of the type of the inorganic fire retardant, other components in the curable resin composition, and a desired degree of fire retardancy. For example, in 100 parts by mass of a curable resin composition containing all the components such as an epoxy resin, a curing agent, a non-halogen fire retardant, filler, and additives, the inorganic fire retardant is preferably added in the range of 0.05 to 20 parts by mass, particularly preferably, in the range of 0.5 to 15 parts by mass.

Examples of the organic metal salt fire retardants include ferrocene, acetylacetonato metal complexes, organic metal carbonyl compounds, organic cobalt salt compounds, organic metal sulfonate salts, and compounds in which metal atoms and aromatic compounds or heterocyclic compounds are bonded through ionic bonds or coordinate bonds.

The amount of such an organic metal salt fire retardant added is appropriately selected on the basis of the type of the organic metal salt fire retardant, other components in the curable resin composition, and a desired degree of fire retardancy. For example, in 100 parts by mass of a curable resin composition containing all the components such as an epoxy resin, a curing agent, a non-halogen fire retardant, another filler, and additives, the organic metal salt fire retardant is preferably added in the range of 0.005 to 10 parts by mass.

A curable resin composition according to the present invention may optionally contain an inorganic filler. Examples of the inorganic filler include fused silica, crystalline silica, alumina, silicon nitride, and aluminum hydroxide. When the amount of such an inorganic filler added is made particularly large, fused silica is preferably used. The fused silica may be used in the form of fragments or spheres. To increase the amount of fused silica added and to suppress an increase in the melt viscosity of the composition, fused silica in the form of spheres is preferably mainly used. To increase the amount of spherical silica added, the size distribution of silica particles is preferably appropriately adjusted. The filling factor of the filler is preferably high in view of fire retardancy and particularly preferably 20 mass % or more relative to the entire amount of the curable resin composition. In applications to conductive paste and the like, a conductive filler such as silver powder or copper powder may be used.

A curable resin composition according to the present invention may optionally contain various additives such as a silane coupling agent, a release agent, a pigment, and an emulsifying agent.

A curable resin composition according to the present invention can be obtained by uniformly mixing the above-described components. A curable resin composition containing an epoxy resin, a curing agent, and optionally a curing accelerator according to the present invention can be readily turned into a cured product by a method similar to known methods. Examples of such cured products are formed cured products such as multilayer products, cast products, adhesive layers, coatings, and films.

Examples of applications of a curable resin composition according to the present invention include printed wiring board materials such as rigid printed wiring board materials, resin compositions for flexible wiring boards, and interlayer insulating materials for build-up boards; semiconductor sealing materials, conductive pastes, adhesive films for build-up, resin casting materials, and adhesives. Of these various applications, in the applications, to rigid printed wiring board materials, insulating materials for electronic circuit boards, and adhesive films for build-up, the curable resin composition can be used as insulating materials for boards within which passive components such as capacitors and active components such as IC chips are embedded, so-called electronic-component built-in boards. Of these, the curable resin composition has characteristics of high fire retardancy, high heat resistance, low thermal expansion, and solvent dissolution properties and hence is preferably used for printed wiring board materials such as rigid printed wiring board materials, resin compositions for flexible wiring boards, and interlayer insulating materials for build-up boards; and semiconductor sealing materials.

Printed wiring boards according to the present invention can be produced by forming the above-described printed wiring board materials in accordance with various applications. Specifically, a rigid printed wiring board may be produced by a method in which a curable resin composition that is in the form of varnish and contains the organic solvent (D) is further mixed with the organic solvent (D) to be turned into varnish, reinforcing bases are impregnated with the varnish and laminated to copper foils, and the resultant laminate is subjected to thermocompression bonding. Examples of the reinforcing bases that are usable herein include paper, glass cloth, glass nonwoven fabric, aramid paper, aramid cloth, glass mat, and glass roving cloth. Such a method will be described in further detail. The curable resin composition that is in the form of varnish is heated to a heating temperature according to the type of a solvent used, preferably to 50 to 170° C., to provide prepregs that are cured products. The proportions of the resin composition and the reinforcing bases by mass that are used herein are not particularly limited, but the proportions are generally preferably adjusted such that the resin content in the prepregs is 20 to 60 mass %. The thus-obtained prepregs are then stacked in a standard manner and appropriately laminated to copper foils and the resultant laminate is subjected to thermocompression bonding under a pressure of 1 to 10 MPa at 170 to 250° C. for 10 minutes to 3 hours to thereby provide a target printed circuit board.

A flexible wiring board is produced from a curable resin composition according to the present invention as follows. The phenol, the epoxy resin (B), the curing accelerator (C), and the organic solvent (ID) are mixed and applied to an electrical insulating film with a coater such as a reverse roll coater or a comma coater. The electrical insulating film is then heated with a heater at 60 to 170° C. for 1 to 15 minutes to evaporate the solvent to thereby bring the adhesive composition into the B-stage. A metal foil is then bonded to the adhesive by thermocompression bonding with a heating roller or the like. At this time, the compression bonding pressure is preferably 2 to 200 N/cm and the compression bonding temperature is preferably 40 to 200° C. When sufficient bonding properties are achieved at this time, the procedure may be finished. When complete curing is required, postcure is preferably further performed under conditions of a temperature of 100 to 200° C. for 1 to 24 hours. The adhesive composition film finally cured preferably has a thickness in the range of 5 to 100 μm.

An interlayer insulating material for build-up boards is produced from a curable resin composition according to the present invention by, for example, the following method. The curable resin composition appropriately containing rubber, filler, and the like is applied to a wiring board in which circuits are formed by a spray coating method, a curtain coating method, or the like and is subsequently cured. Holes are then optionally formed in predetermined through-hole portions and the like. The board is treated with a roughening agent and a surface thereof is rinsed with hot water to thereby form irregularities. The board is plated with a metal such as copper. The plating method is preferably electroless plating or electrolytic plating. Examples of the roughening agent include an oxidizing agent, an alkali, and an organic solvent. Such a procedure is sequentially repeated as needed to alternately build up a resin insulating layer and a conductor layer having a predetermined circuit pattern. As a result, a build-up board can be provided. Note that holes are formed in the through-hole portions after the formation of a resin insulating layer serving as an outermost layer. Alternatively, a build-up board can be produced without the plating step as follows: a copper foil with a resin in which she resin composition is semi-cured on the copper foil is bonded to a wiring board in which circuits are formed by thermocompression bonding at 170 to 250° C. to thereby form a roughened surface.

A semiconductor sealing material according to the present invention can be obtained by sufficiently melt-mixing the phenol (A), the epoxy resin (B), the curing accelerator (C), and additives such as an inorganic filler optionally with an extruder, a kneader, a roller, or the like until uniform mixing is achieved. At this time, the inorganic filler is generally silica. The filling factor of the inorganic filler is preferably in the range of 30 to 95 mass % relative to 100 parts by Mass of the epoxy resin composition; in particular, preferably 70 parts by mass or more to enhance fire retardancy, moisture resistance, and resistance to solder cracking and to decrease linear expansion coefficient; and, to considerably enhance such advantages, 80 parts by mass or more to further enhance the advantages. As for semiconductor package forming, there is a method in which the composition is formed by casting or with a transfer molding apparatus, an injection molding apparatus, or the like and then heated at 50 to 200° C. for 2 to 10 hours to provide formed products serving as semiconductor devices.

As for a method for producing an adhesive film for build-up from a curable resin composition according to the present invention, for example, there is a method in which a curable resin composition according no the present invention is applied to a support film to form a resin composition layer to provide an adhesive film for a multilayer printed wiring board.

When a curable resin composition according to the present invention is used for an adhesive film for build-up, it is important that the adhesive film softens under a lamination temperature condition (generally 70° C. to 140° C.) in a vacuum lamination method and exhibits fluidity (resin flow) with which via holes or through-holes in a circuit board can be filled with the resin at the same time as lamination of the circuit, board. The above-described components are preferably mixed so that such characteristics are exhibited.

Herein, through-holes in multilayer printed wiring boards generally have a diameter of 0.1 to 0.5 mm and a depth of 0.1 to 1.2 mm and through-holes satisfying these ranges are preferably generally filled with the resin. Note that, when lamination is performed on both surfaces of a circuit board, through-holes are desirably filled to about half of the through-holes.

Specifically, the above-described method for producing an adhesive film can be performed as follows. A curable resin composition in the form of varnish according to the present invention is prepared. The varnish composition is then applied to a surface of a support film and the organic solvent is subsequently removed by heating, hot-air blowing, the like to form a layer ($\alpha$) of the curable resin composition.

The formed layer ($\alpha$) generally has a thickness equal to or larger than the thickness of a conductor layer. Since a circuit board generally has a conductor layer with thickness in the range of 5 to 70 μm, the resin composition layer preferably has a thickness of 10 to 100 μm.

Note that the layer ($\alpha$) may be covered with a protective film described below. By protecting the surface of the resin composition layer with a protective film, adhesion of dust or the like and scratching in the surface can be suppressed.

The support film and the protective film may be composed of, for example, a polyolefin such as polyethylene, polypropylene, or polyvinyl chloride; a polyester such as polyethylene terephthalate (hereafter, sometimes abbreviated as PET) or polyethylene naphthalate; polycarbonate; polyimide; release paper; or a metal foil such as a copper foil or an aluminum foil. Note that the support film and the protective film may be subjected to a mud treatment, corona treatment, and a release treatment.

The thickness of the support film is not particularly limited and is generally 10 to 150 μm, preferably in the range of 25 to 50 μm. The protective film preferably has a thickness of 1 to 40 μm.

The above-described support film is released after lamination to a circuit board or after the formation of an insulating layer by heat-curing. By releasing the support film after the adhesion film is heat-cured, adhesion of dust or the like in the curing step can be suppressed. When the support film is released after the curing, the support film is generally subjected to a release treatment in advance.

A method for producing a multilayer printed wiring board with the thus-obtained adhesive film is performed by, for example, in the cases where the layer ($\alpha$) is protected with a protective film, removing the protective film and performing lamination such that the layer ($\alpha$) is in direct contact with a single surface or both surfaces of a circuit board by, for example, a vacuum lamination method. The lamination may be performed by a batch process or a continuous process with rollers. The adhesive film and the circuit board may be optionally heated (preheated) before the lamination.

As for lamination conditions, lamination is preferably performed at a compression bonding temperature (lamination temperature) of 70 to 140° C., at a compression bonding pressure of 1 to 11 kgf/cm$^2$ (9.8×10$^4$ to 107.9×10$^4$ N/m2), and under a reduced air pressure of 20 mmHg (26.7 hPa) or less.

When a curable resin composition according to the present invention is used as a conductive paste, for example, there are a method in which fine conductive particles are dispersed in the curable resin composition to provide a composition for an anisotropic conductive film and a method in which the curable resin composition is turned into a resin composition paste for circuit connection or an anisotropic conductive adhesive, the resin composition paste and the anisotropic conductive adhesive being in the form of liquid at room temperature.

The method for providing a cured product according to the present invention may be performed by appropriately selecting heating-temperature conditions or the like in accordance with the type of a curing agent combined, an application, or the like. For example, there is a method in which the composition obtained by the above-described method is cured in a temperature range of about 20 to 250° C.

As has been described so far in detail, by using a phosphorus-containing phenolic compound according to the present invention, solvent dissolution properties considerably enhance, compared with existing phosphorus-modified phenolic resins; and, in the form of a cured product, fire retardancy, heat resistance, and heat resistance reliability can be exhibited and applications to the most advanced printed wiring board materials can be achieved. In addition, the phenolic resin can be efficiently readily produced by a production method according to the present invention and molecular design according to the level of the target properties can be performed.

EXAMPLES

Hereinafter, the present invention will be specifically described with reference to EXAMPLES and COMPARATIVE EXAMPLES. Note that melt viscosity at 180° C., GPC measurement, NMR, and MS spectra were measured under the following conditions
1) Melt viscosity as 180° C.: compliance with ASTM D4287
2) Softening-point measurement method: JIS K7234
3) CPC: measurement conditions are as follows.
  Measurement apparatus: "HLC-8220 GPC", manufactured by Tosob. Corporation
  Columns: guard column "HXL-L", manufactured by Tosoh Corporation,
    +"TSK-GEL G2000HXL", manufactured by Tosoh Corporation,
    +"TSK-GEL G2000HXL", manufactured by Tosoh Corporation,
    +"TSK-GEL G3000HXL", manufactured by Tosoh Corporation,
    +"TSK-GEL G4000HXL", manufactured by Tosob Corporation
  Detector: RI (differential refractive index diameter)
  Data processing: "GPC-8020 Model II version 4.10", manufactured by Tosoh Corporation.
  Measurement conditions: column temperature 40° C.
  developing solvent tetrahydrofuran
  flow rate 1.0 ml/min
  Standards: the following monodisperse polystyrenes whose molecular weights are known were used in compliance with the measurement manual of the "GPC-8020 Model 11 version 4.10" (Used polystyrenes)
    "A-500", manufactured by Tosoh Corporation
    "A-1000", manufactured by Tosoh Corporation "A-2500", manufactured by Tosoh Corporation
"A-5000", manufactured by Tosoh Corporation
"F-1", manufactured by Tosoh Corporation
"F-2", manufactured by Tosoh Corporation
"F-4", manufactured by Tosoh Corporation
"F-10", manufactured by Tosoh Corporation
"F-20", manufactured by Tosoh Corporation
"F-40", manufactured by Tosoh Corporation
"F-80", manufactured by Tosoh Corporation
"F-128", manufactured by Tosoh Corporation Samples: solutions (50 µl) obtained by filtrating a 1.0 mass % tetrahydrofuran solution in terms OT resin solid matter through a microfilter,
5) NMR: NMR GSX270, manufactured by JEOL Ltd.
6) MS: Double focusing mass spectrometer AX505H (FD505H), manufactured by JEOL Ltd.

Example 1

Synthesis of Phenolic Resin (A-1)

A flask equipped with a thermometer, a condenser, a fractional distillation column, a nitrogen-gas inlet tube, and a stirrer was charged with 192.4 g (1.85 mol) of a phenolic novolac resin, 68.0 g (0.50 mol) of p-anisic aldehyde, and 108.0 g (0.50 mol) of 9,10-dihydro-9-oxa-10-phosphaphenanthrene-10-oxide (hereafter, abbreviated as "HCA") and heated to 180° C. to allow reaction to proceed at 180° C. for 8 hours. Water was then removed under heating and a reduced pressure to provide 355 g of a phenolic resin (A-1) having, as repeating units, the following structural units A and B.

[Chemical formula 35]

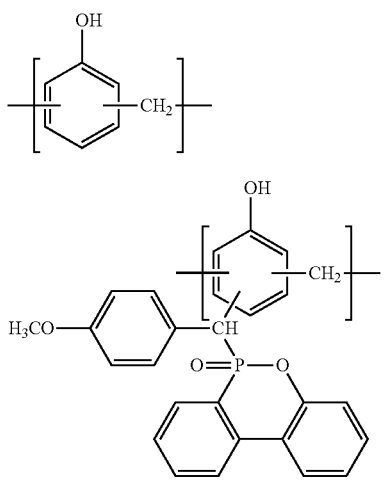

The resultant phenolic resin had a softening point of 125° C. (B&R method), a melt viscosity (measurement method: ICI viscometer method, measurement temperature: 180° C.) of 13 dPa·s, a hydroxy equivalent of 190 g/eq, and a phosphorus content of 4.2 mass %.

The GPC chart of the obtained phenolic resin (A-1) is illustrated in FIG. 1, the C13 NMR chart in FIG. 2, and the MS spectrum in FIG. 3.

Example 2

Synthesis of Phenolic Resin (A-2)

Synthesis was performed as in EXAMPLE 1 except that the amount of the phenolic novolac resin was changed to 136.6 g (1.31 mol) to provide 290 g of a phenolic resin (A-2) having, as repeating units, the following structural units A and B.

[Chemical formula 36]

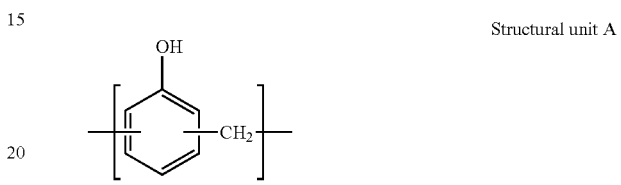

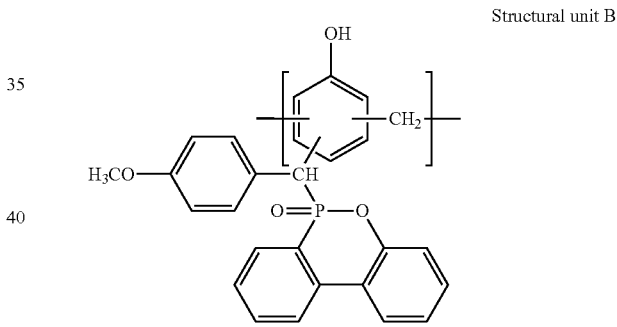

The resin had a softening point of 148° C. (B&R method), a melt viscosity (measurement method: ICI viscometer method, measurement temperature: 180° C.) of 400 dPa·s, a hydroxy equivalent of 230 g/eq, and a phosphorus content of 4.9 mass %.

The GPC chart of the obtained phenolic resin (A-2) is illustrated in FIG. 4.

Example 3

Synthesis of Phenolic Resin (A-3)

Synthesis was performed as in EXAMPLE 1 except that the phenolic novolac resin was changed to 330.4 g (2.80 mol) of a bisphenol A novolac resin to provide 490 g of a phenolic resin (A-3) having, as repeating units, the following structural units C and D.

[Chemical formula 37]

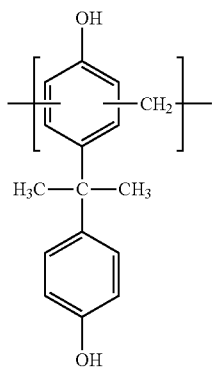
Structural unit C

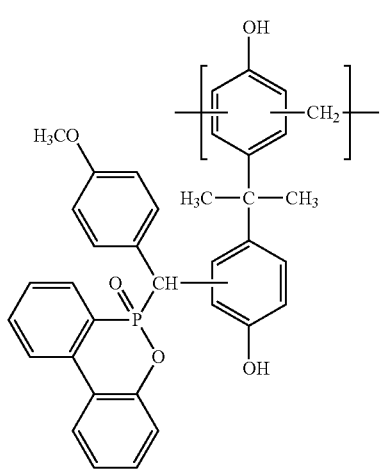
Structural unit D

The resin had a softening point of 139° C. (B&R method), a melt viscosity (measurement method: ICI viscometer method, measurement temperature: 180° C.) of 65 dPa·s, a hydroxy equivalent, of 232 g/eq, and a phosphorus content of 3.1 mass %.

Figure 5:
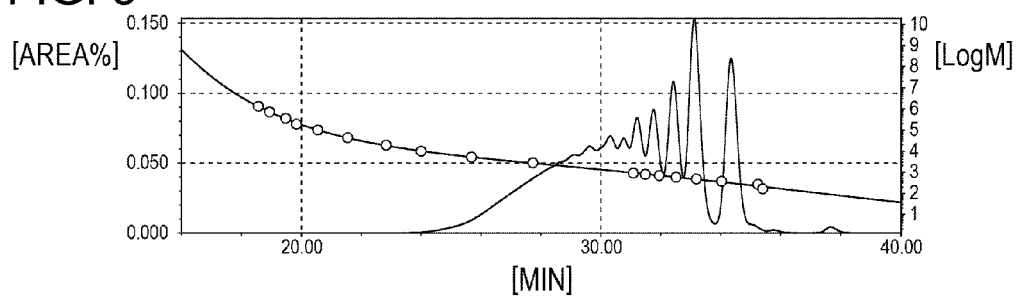
FIG. 5 illustrates a GPC chart of a phenolic resin (A-3) obtained in EXAMPLE 3.

The GPC chart of the obtained phenolic resin (A-3) is illustrated in FIG. 5.

Example 4

Synthesis of Phenolic Resin (A-4)

Synthesis was performed as in EXAMPLE 1 except that the phenolic novolac resin was changed to 392.9 g (2.35 mol) of a phenyl aralkyl resin to provide 550 g of a phenolic resin (A-4) having, as repeating units, the following structural units E and F.

[Chemical formula 38]

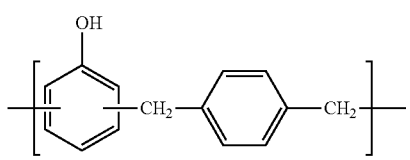
Structural unit E

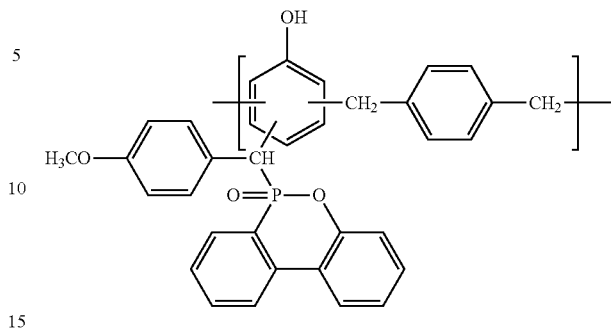
Structural unit F

Figure 6:
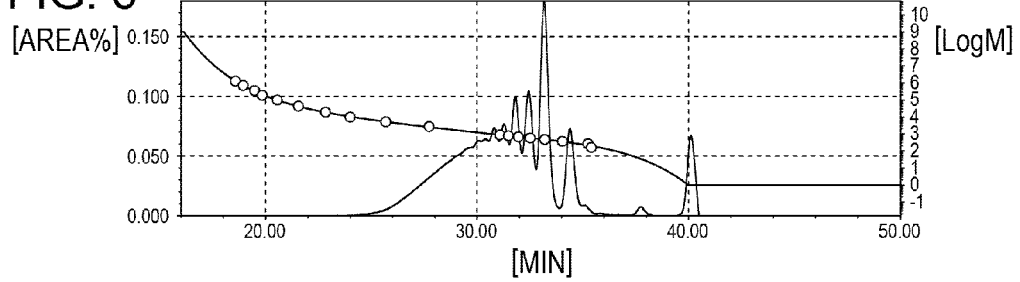
FIG. 6 illustrates a GPC chart of a phenolic resin (21-4) obtained in EXAMPLE 4.

The resultant phenolic resin had a softening point of 102° C. (E&R method), a melt viscosity (measurement method: ICI viscometer method, measurement temperature: 150° C.) of 2.5 dPa·s, a hydroxy equivalent of 232 g/eq, and a phosphorus content of 2.7 mass %. The GPC chart of the obtained phenolic resin (A-4) is illustrated in FIG. 6.

Example 5

Synthesis of Phenolic Resin (A-5)

Synthesis was performed as in EXAMPLE 4 except that the parts by weight of the phenyl aralkyl resin was changed to 211.25 g (1.25 mol) to provide 370 g of a phenolic resin (A-5) having, as repeating units, the following structural units E and F.

[Chemical formula 39]

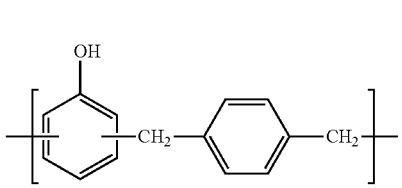
Structural unit E

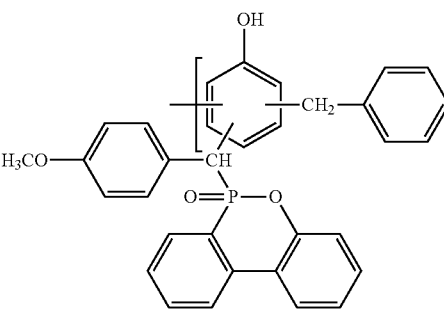
Structural unit F

The resin had a softening point of 140° C. (B&R method), a melt viscosity (measurement method: ICI viscometer method, measurement temperature: 150° C.) of 50 dPa·s, a hydroxy equivalent of 303 g/eq, and a phosphorus content of 4.5 mass %.

Figure 7:
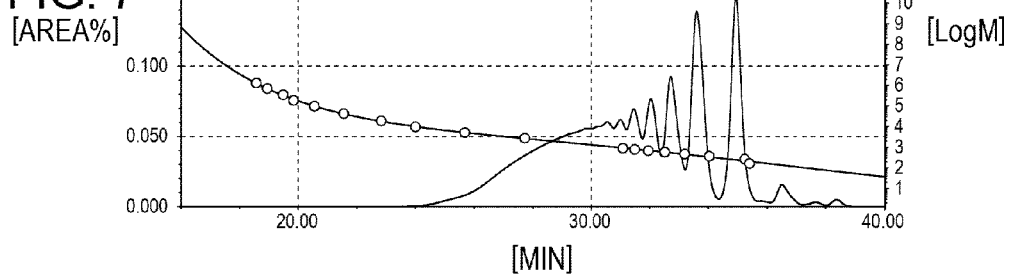
FIG. 7 illustrates a GPC chart of a phenolic resin (21-5) obtained in EXAMPLE 5.

The GPC chart of the obtained phenolic resin (A-5) is illustrated in FIG. 7.

Example 6

Synthesis of Phenolic Compound (A-6)

A flask equipped with a thermometer, a condenser, a fractional distillation column, a nitrogen-gas inlet tube, and a stirrer was charged with 200 g (1.0 mol) of bisphenol F, 136 g (1.0 mol) of p-anisic aldehyde, and 216 g (1.0 mol) of RCA and heated to 180° C. to allow reaction to proceed at 180° C. for 8 hours. Water was then removed under heating and a reduced pressure to provide 520 g of a phenolic compound. (A-6) having a structural unit represented by the following structural formula.

[Chemical formula 40]

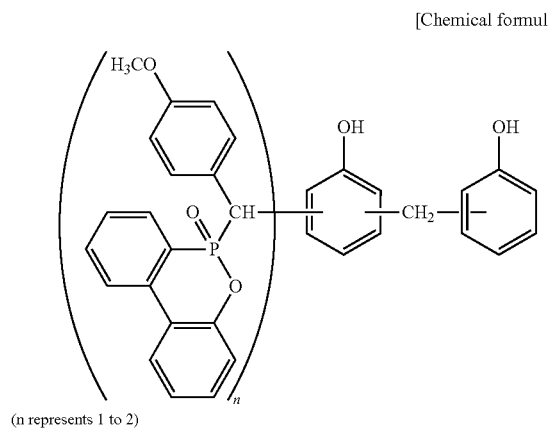

(n represents 1 to 2)

Figure 8:
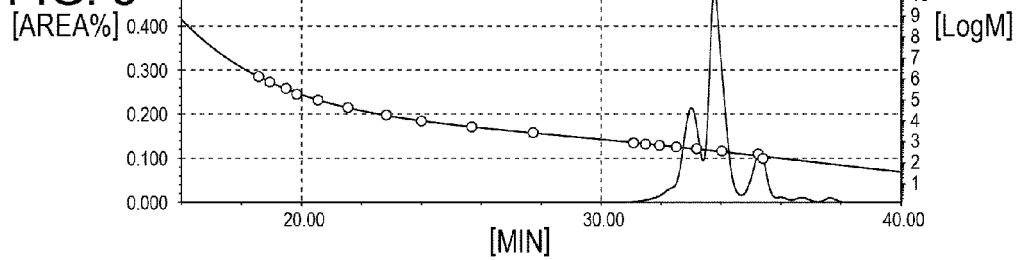
FIG. 8 illustrates a GPC chart of a phenolic compound (A-6) obtained in EXAMPLE 6.

The GPC chart of the obtained polyhydric hydroxy compound is illustrated in FIG. 8. The phosphorus content was 5.6 mass %.

Example 7

Synthesis of Phenolic Compound (A-7)

Synthesis was performed as in EXAMPLE 6 except that the bisphenol F was changed to 110 g (1.0 mol) of resorcinol to provide 440 g of a phenolic compound (A-7) having structural unit represented by the following formula.

[Chemical formula 41]

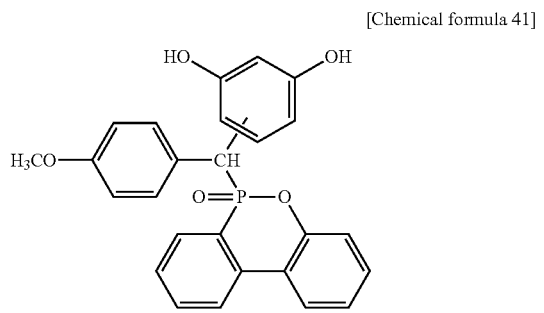

Figure 9:
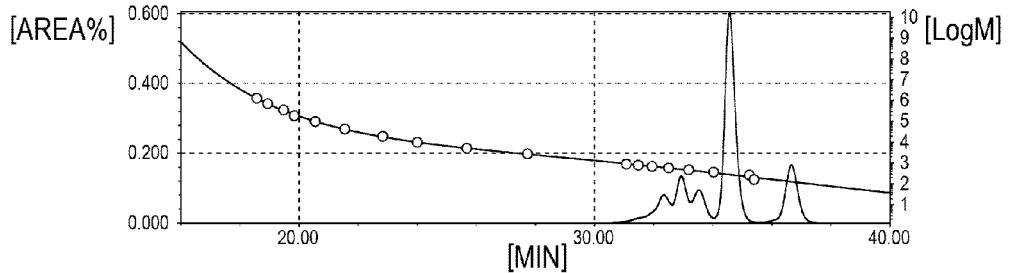
FIG. 9 illustrates a GPC chart of a phenolic compound (A-7) obtained in EXAMPLE 7.

The GPC chart of the obtained phenolic compound (A-7) is illustrated in FIG. 9. The phosphorus content was 6.7 mass %.

Example 8

Synthesis of Phenolic Compound (A-8)

Synthesis was performed as in EXAMPLE 6 except that the bisphenol F was changed to 160 g (1.0 mol) of 2,7-dihydroxynaphthalene to provide 490 g of a phenolic compound (A-8) having a structural unit represented by the following formula.

[Chemical formula 42]

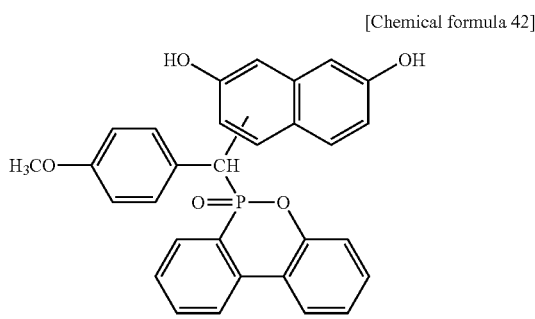

Figure 10:
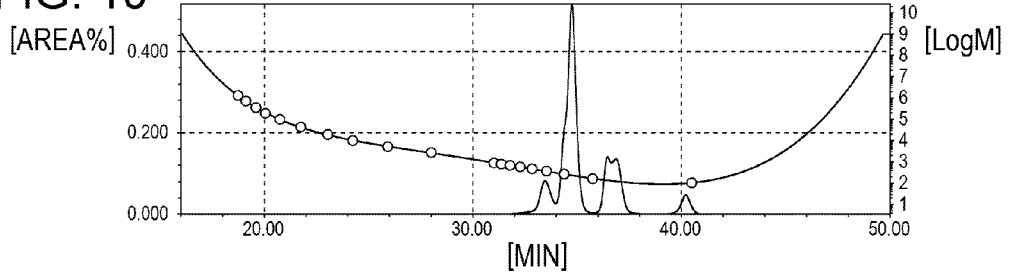
FIG. 10 illustrates a GPC chart of a phenolic compound (A-8) obtained in EXAMPLE 8.

The GPC chart of the phenolic compound (A-8) is illustrated in FIG. 10. The phosphorus content was 6.3 mass %.

Synthesis Example 1

Synthesis of Compound Described in Patent Literature 1 (Japanese Patent No. 3464783) Above A reaction vessel was charged with 216 g (1.0 mol) of HCA and 71 g (1.0 mol) of a 42 mass % formalin and heated to 100° C. to allow reaction to proceed for 4 hours. A precipitated solid was collected by filtration and washed with acetone to provide 245 g of 2-(6-oxide-6H-dibenz<c,e><1,2>oxa-phosphorin-6-yl)methanol (hereafter, referred to as ODOPM). The obtained compound has a melting point of 152 to 154° C.

Synthesis Example 2

Figure 11:
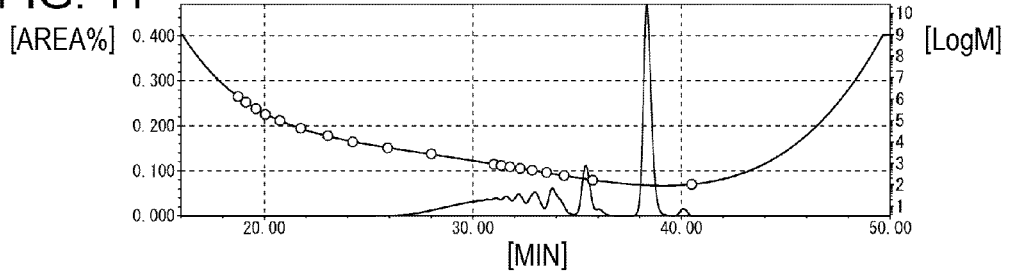
FIG. 11 illustrates a GPC chart of a phenolic resin (A-9) obtained in SYNTHESIS EXAMPLE 2.

Synthesis of Compound (Phenolic Resin (A-9))
Described in Patent Literature 1 (Japanese Patent No. 3464783) Above A recovery flask was charged with 144 g (1.0 mol) of a phenolic novolac resin and heated to 00° C. under stirring and nitrogen flow. After the temperature increase, the resin was mixed with 230 g (1.0 mol) of ODOPM, heated to 140° C., and maintained for 12 hours. The mixture was then cooled to room temperature, filtrated, and dried to provide a phenolic resin (A-9). The GPC chart of the phenolic resin (A-9) is illustrated in FIG. 11.

Synthesis Example 3

Synthesis of Phenolic Compound (Phenolic Compound (A-10)) Described in Patent Literature 2 (Japanese Patent No. 3476730) Above A flask equipped with a thermometer, a condenser, a fractional distillation column, a nitrogen-gas inlet tube, and a stirrer was charged with 216 g (1.0 mol) of HCA and 216 g of toluene and heated to 110° C. to dissolve HCA under heating. The flask was further charged with 122 g (1.0 mol) of p-hydroxybenzaldehyde and heated to 180° C. to allow reaction to proceed at 180° C. for 3 hours. The mixture was then filtrated and dried to provide 335 g of a phenolic compound (A-10) represented by the following structural formula.

[Chemical formula 43]

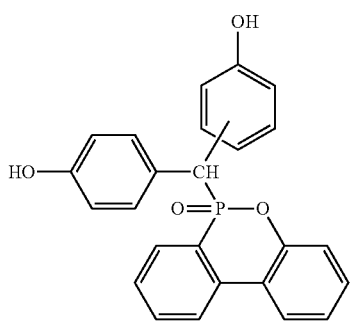

Figure 12:
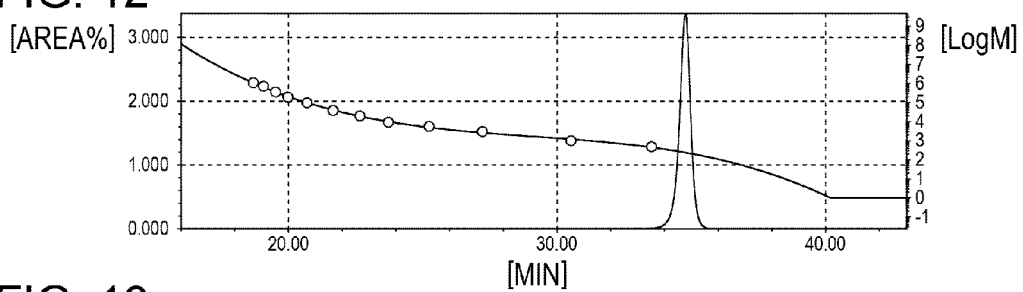
FIG. 12 illustrates a GPC chart of a phenolic compound (A-10) obtained in SYNTHESIS EXAMPLE 3.

The obtained phenolic compound (A-11) had a melting point, of 286° C. The GPC chart of the obtained phenolic compound is illustrated in FIG. 12.

Synthesis Example 4

Synthesis of Phenolic Resin (A-11)

A flask equipped with a thermometer, a condenser, a fractional distillation column, a nitrogen-gas inlet tube, and a stirrer was charged with 457.6 g (1.1 mol) of a phenolic novolac resin, 216 g (1.0 mol), and 122 g (1.0 mol) of p-hydroxybenzaldehyde, and heated to 180° C. to allow reaction to proceed at 180° C. for 8 hours. Water was removed under heating and a reduced pressure to provide 750 g of a phenolic resin (A-11) having repeating units represented by the following structural units G and H.

[Chemical formula 44]

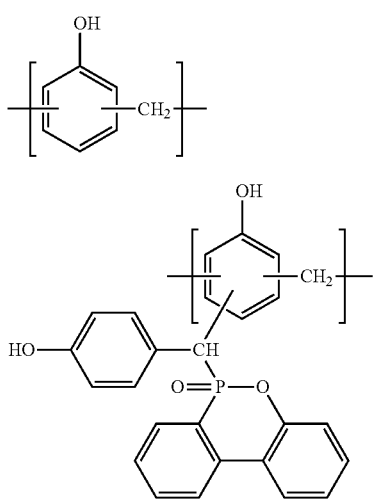

Structural unit G

Structural unit H

Figure 13:
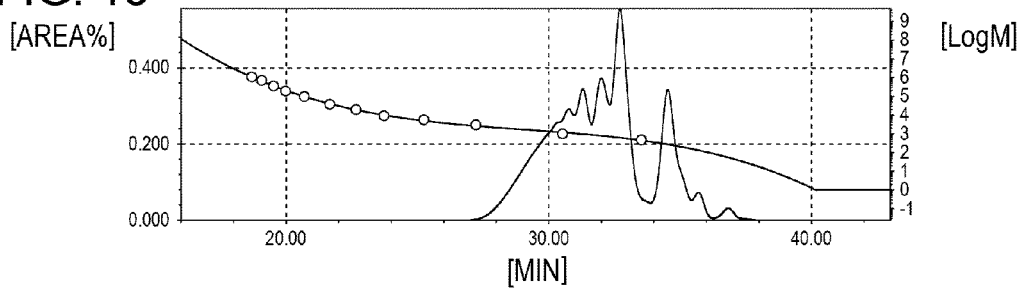
FIG. 13 illustrates a GPC chart of a phenolic resin (A-11) obtained in SYNTHESIS EXAMPLE 4.

The resultant phenolic resin had a softening point of 150° C. (B&R method), a melt viscosity (measurement method: ICI viscometer method, measurement temperature: 150° C.) of 120 dPa·s, a hydroxy equivalent of 164 g/eq, and a phosphorus content of 3.7 mass %. The GPC chart of the obtained phenolic resin (A-11) is illustrated in FIG. 13.

Examples 9 to 13 and Comparative Examples 1 to 4

Epoxy resin compositions were adjusted in accordance with formulations described in Table 1 by a method described below and then cured to experimentally produce multilayer plates. The multilayer plates were subjected to various evaluations. The results are described in Table 1.

[Adjustment of Epoxy Resin Compositions]

Epoxy resins, curing agents, and other components were mixed in accordance with formulations described in Table 1 and then adjusted such that the non-volatile content (N. V.) of the compositions was finally 58 mass %.

[Multilayer Plate Production Conditions]

Base: 100 μm; glass cloth "#2116" manufactured by Nitta Boseki Co., Ltd.

Number of plies: 6

Conditions for forming prepreg: 160° C./2 min

Copper foil: 18 μm; JTC foil manufactured by Nippon Mining & Metals Co., Ltd.

Curing conditions: 200° C., 40 kg/cm2, 1.5 hours

Thickness of formed plate: 0.8 mm

[Physical Property Test Conditions]

Glass transition temperature: measured by TMA method (compressive stress method) after an etching treatment was performed to remove a copper foil. Temperature increase rate: 10° C./min Combustion test: the test method was in compliance with UL-94 vertical test.

Thermal delamination test (time to delamination): Evaluation in terms of thermal delamination properties (with a copper foil) at 288° C. was performed in compliance with IPC TM650.

Thermal decomposition temperature: The temperature at which weight decreased by 5% was determined by TGA.

Temperature increase rate: 10° C./min (in a dry air atmosphere)

[Table 1]

TABLE 1

| | | Examples | | | | | Comparative examples | | | |
|---|---|---|---|---|---|---|---|---|---|---|
| | | 9 | 10 | 11 | 12 | 13 | 1 | 2 | 3 | 4 |
| Epoxy resin | N-770 | 62 | 62 | 62 | 62 | 62 | 74 | 74 | 74 | |
| | FX-289BEK75 | | | | | | | | | 114 |
| Curing agent | A-1 | 63 | | | | | | | | |
| | A-2 | | 76 | | | | | | | |

TABLE 1-continued

|  |  | Examples | | | | | Comparative examples | | | |
| --- | --- | --- | --- | --- | --- | --- | --- | --- | --- | --- |
|  |  | 9 | 10 | 11 | 12 | 13 | 1 | 2 | 3 | 4 |
|  | A-3 |  |  | 77 |  |  |  |  |  |  |
|  | A-4 |  |  |  | 77 |  |  |  |  |  |
|  | A-5 |  |  |  |  | 101 |  |  |  |  |
|  | A-9 |  |  |  |  |  | 42 |  |  |  |
|  | A-10 |  |  |  |  |  |  | 68 |  |  |
|  | A-11 |  |  |  |  |  |  |  | 66 |  |
|  | TD-2090 |  |  |  |  |  |  |  |  | 36 |
| Curing accelerator | 2E4MZ (wt %) | 0.05 | 0.1 | 0.1 | 0.1 | 0.1 | 0.1 | 0.1 | 0.1 | 0.1 |
| Organic solvent | MEK | 90 | 100 | 100 | 100 | 118 | 84 | 103 | 101 | 109 |
| Glass transition temperature (TMA) (° C.) |  | 158 | 163 | 152 | 139 | 141 | 145 | Not evaluated due to crystal precipitation | 187 | 129 |
| 5% weight decrease temperature (TG) |  | 350 | 350 | 350 | 350 | 350 | <310 |  | <310 | <310 |
| Thermal decomposition resistance (T288) (min) |  | >60 | >60 | >60 | >60 | >60 | 0 |  | 0 | 0 |
| Fire retardancy | Maximum combustion time (s) | 9 | 8 | 9 | 9 | 8 | Up to clamp |  | Up to clamp | 9 |
|  | Total combustion time (s) | 48 | 20 | 47 | 44 | 32 | — |  | — | 45 |
|  | Combustion test class | V-0 | V-0 | V-0 | V-0 | V-0 | Combustion |  | Combustion | V-0 |

Abbreviations in Table 1 are as follows.

"A-1": phenolic resin (A-1) obtained in EXAMPLE 1

"A-2": phenolic resin (A-2) obtained in EXAMPLE 2

"A-3": phenolic resin (A-3) obtained in EXAMPLE 3

"A-4": phenolic resin (A-4) obtained in EXAMPLE 4

"A-5": phenolic resin (A-5) obtained in EXAMPLE 5

"A-9": phenolic resin (A-9) obtained in SYNTHESIS EXAMPLE 2

"A-10": phenolic compound (A-10) obtained in SYNTHESIS EXAMPLE 3

"A-11": phenolic resin (A-11) obtained in SYNTHESIS EXAMPLE 4

"TD-2090": phenolic novolac resin ("TD-2090", manufactured by DIC Corporation, hydroxy equivalent: 105 g/eq), "N-770": phenolic novolac epoxy resin ("N-770", manufactured by DIC Corporation, epoxy equivalent: 185 g/eq), "FX-289BER75": phosphorus-modified epoxy resin ("FX-289BER75", manufactured by Tohto Kasei Co., Ltd.: epoxy resin obtained by reaction between a cresol novolac epoxy resin and 9,10-dihydro-9-oxa-10-phosphaphenanthrene-10-oxide, epoxy equivalent: 330 g/eq, and phosphorus content: 3.0 mass %)

The invention claimed is:

1. A novel phenolic compound having a chemical structure represented by a structural formula (I) below:

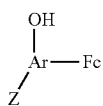

I wherein, in the structural formula (I), Ar represents a benzene ring or a naphthalene ring; Fc represents a hydrogen atom or a hydroxy group; and Z represents a structural unit represented by a structural formula z1 below:

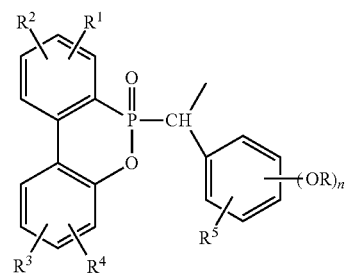

z1 wherein, in the structural formula z1, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents a number of a substituent OR on an aromatic nucleus and is 1 to 3.

2. A novel phenolic resin having a novolac phenolic resin structure and having, as a substituent on an aromatic nucleus of the resin structure, a structural unit represented by a structural formula z1 below:

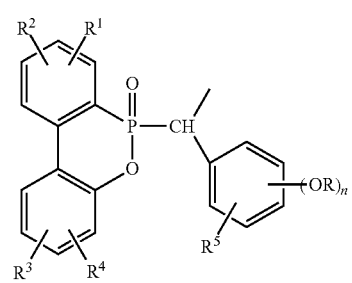

z1 wherein, in the structural formula z1, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents a number of a substituent OR on an aromatic nucleus and is 1 to 3.

3. A novel phenolic resin comprising, as a repeating unit, a structure represented by a structural formula (II) below:

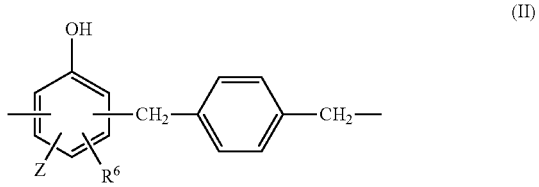
(II)

wherein, in the structural formula (II), $R^6$ represents a hydrogen atom or an alkyl group having 1 to 6 carbon atoms; and Z is selected from the group consisting of a hydrogen atom and a structural formula z1 below:

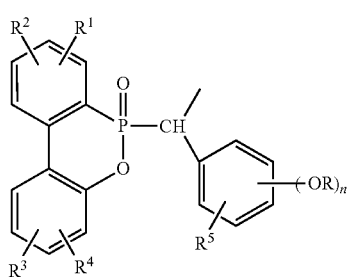
z1 wherein, in the structural formula z1, $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; $R^5$ represents a hydrogen atom or an alkyl group having 1 to 5 carbon atoms; R represents an alkyl group having 1 to 4 carbon atoms; and n represents a number of a substituent OR on an aromatic nucleus and is 1 to 3 and, in the novel phenolic resin, at least one Z has a structural unit selected from partial structures represented by the structural formula z1.

4. A curable resin composition comprising a phenolic compound or phenolic resin (A) and an epoxy resin (B) as essential components, wherein the phenolic compound or phenolic resin (A) is the novel phenolic compound or phenolic resin according to claim 1, 2, or 3.

5. The curable resin composition according to claim 4, comprising the phenolic compound or phenolic resin (A) and the epoxy resin (B) such that an amount of active hydrogen in the phenol (A) is 0.7 to 1.5 equivalents per equivalent of epoxy groups in total of the epoxy resin (B).

6. A cured product provided by curing the curable resin composition according to claim 4.

7. The curable resin composition according to claim 4, comprising, in addition to the phenolic compound or phenolic resin (A) and the epoxy resin (B), a curing accelerator (C).

8. A semiconductor sealing material comprising the curable resin composition according to claim 7 and an inorganic filler.

9. A varnish comprising the curable resin composition according to claim 7, and an organic solvent (D).

10. A printed wiring board comprising a cured varnish, wherein the varnish according to claim 9 is used.

11. A method for producing a phosphorus-containing phenol-based substance comprising allowing an aromatic aldehyde (a1) having an alkoxy group as a substituent on an aromatic nucleus to react with an organic phosphorus compound (a2) represented by a structural formula (A2-a) below:

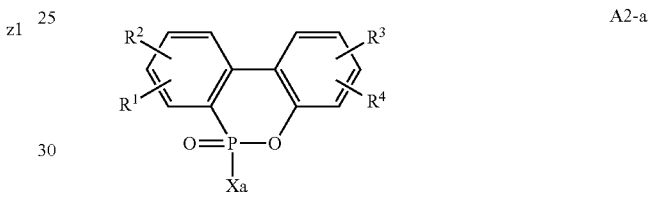
A2-a wherein, in the structural formula (A2-a), $R^1$, $R^2$, $R^3$, and $R^4$ each independently represent a hydrogen atom, an alkyl group having 1 to 5 carbon atoms, a chlorine atom, a bromine atom, a phenyl group, or an aralkyl group; and Xa represents a hydrogen atom; and subsequently allowing a resultant reaction product to react with a phenolic compound or phenolic resin (a3).

12. The production method according to claim 11, wherein the aromatic aldehyde (a1) has, as the alkoxy group in the aromatic aldehyde (a1), a methoxy group or an ethoxy group.

13. The production method according to claim 11, wherein the phenolic compound or phenolic resin (a3) is a dihydric phenol.

14. The production method according to claim 13, wherein the dihydric phenol is dihydroxynaphthalene.

15. The production method according to claim 11, wherein the phenolic compound or phenolic resin (a3) is a novolac phenolic resin or an aralkyl phenolic resin.

* * * * *